United States Patent
Arora et al.

(10) Patent No.: US 9,783,526 B2
(45) Date of Patent: *Oct. 10, 2017

(54) CONTROL OF HYPOXIA-INDUCIBLE GENE EXPRESSION WITH OLIGOOXOPIPERAZINE NONPEPTIDIC HELIX MIMETICS

(71) Applicant: New York University, New York, NY (US)

(72) Inventors: Paramjit S. Arora, Cold Spring Harbor, NY (US); Brooke Bullock Lao, Leesville, SC (US)

(73) Assignee: New York University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/018,130

(22) Filed: Feb. 8, 2016

(65) Prior Publication Data

US 2016/0297802 A1 Oct. 13, 2016

Related U.S. Application Data

(63) Continuation of application No. 14/379,450, filed as application No. PCT/US2013/026722 on Feb. 19, 2013, now Pat. No. 9,255,086.

(60) Provisional application No. 61/599,763, filed on Feb. 16, 2012.

(51) Int. Cl.
*A61K 31/496* (2006.01)
*C07D 403/06* (2006.01)
*C07D 403/14* (2006.01)
*C07D 241/08* (2006.01)
*C12N 15/63* (2006.01)

(52) U.S. Cl.
CPC .......... *C07D 403/06* (2013.01); *A61K 31/496* (2013.01); *C07D 241/08* (2013.01); *C07D 403/14* (2013.01); *C12N 15/63* (2013.01)

(58) Field of Classification Search
CPC .................................................. C07D 403/06
USPC ...................... 514/252.11; 544/357; 435/375
See application file for complete search history.

(56) References Cited

U.S. PATENT DOCUMENTS

| 8,791,121 B2 | 7/2014 | Arora et al. | |
| 9,255,086 B2 | 2/2016 | Arora et al. | |
| 9,309,230 B2 * | 4/2016 | Arora | C07D 241/08 |
| 2003/0191049 A1 | 10/2003 | Amblard et al. | |
| 2015/0072991 A1 | 3/2015 | Arora et al. | |
| 2016/0214965 A1 * | 7/2016 | Arora | C07D 241/08 |

FOREIGN PATENT DOCUMENTS

| WO | 9620173 A1 | 7/1996 |
| WO | 0151506 A2 | 7/2001 |
| WO | 2012021144 A1 | 2/2012 |

OTHER PUBLICATIONS

PCT International Search Report and Written Opinion for PCT/US2013/026722, mailed Jul. 1, 2013.
Dames et al., "Structural Basis for Hif-1α/CBP Recognition in the Cellular Hypoxic Response," Proc. Nat'l Acad. Sci. 99(8):5271-76 (2002).
Freedman et al., "Structural Basis for Recruitment of CBP/p300 by Hypoxia-Inducible Factor-1α," Proc. Nat'l Acad. Sci. 99(8):5367-72 (2002).
Hirota & Semenza, "Regulation of Angiogenesis by Hypoxia-Inducible Factor 1," Crit. Rev. Oncol./Hematol. 59:15-26 (2006).
Semenza, "Targeting HIF-1 for Cancer Therapy," Nat. Rev. Cancer 3:721-32 (2003).
Tosovská & Arora, "Oligooxopiperazines as Nonpeptidic α-Helix Mimetics," Org. Lett. 12(7):1588-91 (2010).
Extended European Search Report for corresponding European Patent Application No. 13749783.0 (Sep. 30, 2015).

* cited by examiner

*Primary Examiner* — Kristin Vajda
(74) *Attorney, Agent, or Firm* — LeClairRyan, a Professional Corporation

(57) ABSTRACT

The present invention relates to oligooxopiperazines that mimic helix αB of the C-terminal transactivation domain of HIF-1α. Also disclosed are pharmaceutical compositions containing these oligooxopiperazines and methods of using these oligooxopiperazines (e.g., to reduce gene transcription, treat or prevent disorders mediated by interaction of HIF-1α with CREB-binding protein and/or p300, reduce or prevent angiogenesis in a tissue, induce apoptosis, and decrease cell survival and/or proliferation).

11 Claims, 19 Drawing Sheets

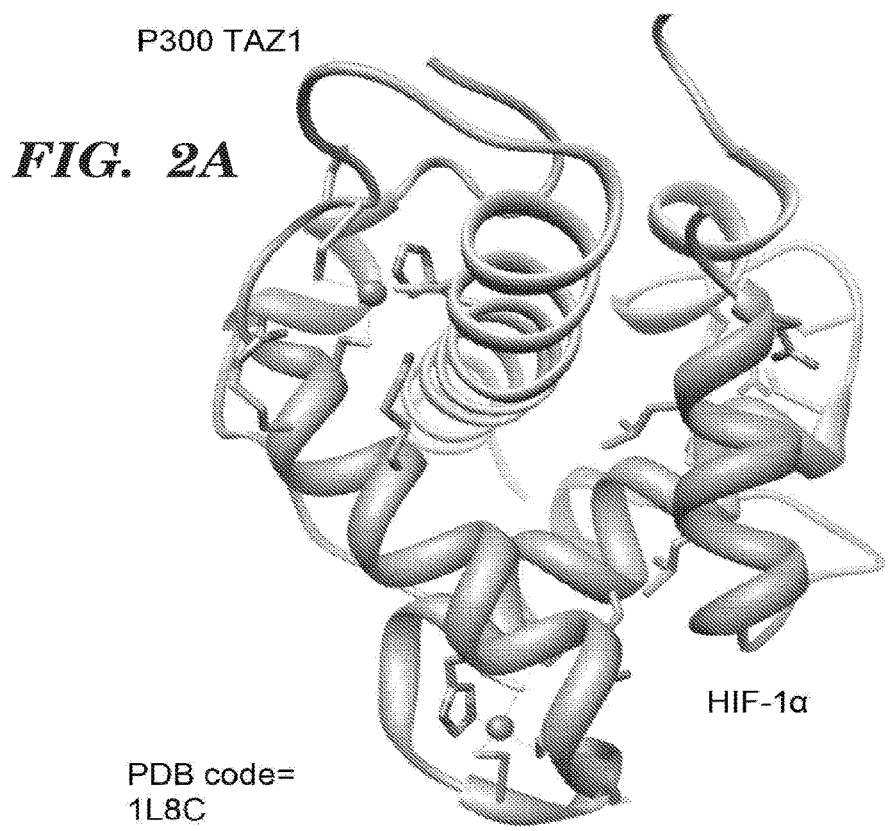
*FIG. 2A*
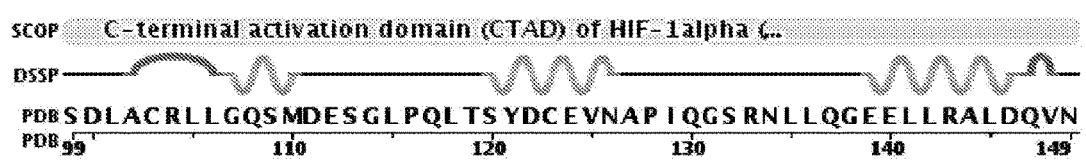
*FIG. 2B*
| Residue | Helix residue | PDB residue | Helix position | ΔΔG (kcal/mol) |
|---------|---------------|-------------|----------------|----------------|
| Leu | 818 | 141 | $i$ | 2.4 |
| Leu | 822 | 145 | $i+4$ | 2.2 |
| Gln | 824 | 147 | $i+6$ | 1.3 |
*FIG. 2C*

CONTROL OF HYPOXIA-INDUCIBLE GENE EXPRESSION WITH OLIGOOXOPIPERAZINE NONPEPTIDIC HELIX MIMETICS

This application is a continuation of U.S. patent application Ser. No. 14/379,450, filed Aug. 18, 2014, which is a national stage application under 35 U.S.C. §371 from PCT Application No. PCT/US2013/026722, filed Feb. 19, 2013, which claims the benefit of U.S. Provisional Patent Application Ser. No. 61/599,763, filed Feb. 16, 2012, which is hereby incorporated by reference in its entirety.

This application claims the benefit of U.S. Provisional Patent Application Ser. No. 61/599,763, filed Feb. 16, 2012, which is hereby incorporated by reference in its entirety.

FIELD OF THE INVENTION

The present invention relates to oligooxopiperazines that include a sequence that substantially mimics helix αB of the C-terminal transactivation domain of Hypoxia-Inducible Factor 1α.

BACKGROUND OF THE INVENTION

As illustrated in FIG. 1, angiogenesis, the induction of new blood vessels, is critical for normal growth as well as pathogenesis of various disorders. In cancers, angiogenesis accelerates growth of solid tumors and provides a gateway to metastasis via the newly formed vasculature. In contrast, therapeutic angiogenesis is important for reducing the effects of tissue ischemia and preventing organ failure. The process of angiogenesis is tightly controlled by a number of specific mitogens, among which vascular endothelial growth factor (VEGF) and its receptors play a key role. The levels of VEGF are upregulated across a broad range of tumors, and play a causal role in oncogenic signaling. In cells and tissues, transcription of VEGF gene is regulated by hypoxia-inducible factors. Among them, Hypoxia-Inducible Factor 1 ("HIF-1") is the main regulator of oxygen-dependent transcription in a majority of organs and accounts for the increase in expression of hypoxia-inducible genes. HIF-1 consists of an oxygen-sensitive a and a constitutively expressed β subunit. Under well-oxygenated conditions, HIF-1α is hydroxylated (Ivan et al., "HIFα Targeted for VHL-mediated Destruction by Proline Hydroxylation: Implications for $O_2$ Sensing," Science 292:464-8 (2001)), ubiquitinated, and degraded by the ubiquitin—proteasome system. Under hypoxia, HIF-1α is stabilized and translocates into the nucleus where heterodimerization with its constitutively expressed binding partner, aryl hydrocarbon receptor nuclear translocator ("ARNT") (Wood et al., "The Role of the Aryl Hydrocarbon Receptor Nuclear Translocator (ARNT) in Hypoxic Induction of Gene Expression," J. Biol. Chem. 271:15117-23 (1996)) results in binding to a cognate hypoxia response element ("HRE") (Forsythe et al., "Activation of Vascular Endothelial Growth Factor Gene Transcription by Hypoxia-inducible Factor 1," Mol. Cell. Biol. 16:4604-13 (1996)). The heterodimer then recruits transcriptional coactivators, p300, CBP, and SRC-1, resulting in the upregulation of the hypoxia-inducible genes. Regulation of the activity of hypoxia-inducible factors includes three critical steps: (i) inhibition of hydroxylation of two proline residues to preclude interaction of HIF-1α with pVHL, a part of ubiquitin ligase complex, thereby preventing its proteasomal destruction; (ii) inhibition of hydroxylation of Asn803 by Factor Inhibiting HIF-1α ("FIH") (Lando et al., "FIH-1 Is an Asparaginyl Hydroxylase Enzyme That Regulates the Transcriptional Activity of Hypoxia-inducible Factor," Genes & Develop. 16:1466-71 (2002)) to enable recruitment of coactivators, which trigger overexpression of hypoxia inducible genes, including genes encoding angiogenic peptides such as VEGF and VEGF receptors VEGFR-1 (Flt-1) and VEGFR-2 (KDR/Flk-1), as well as proteins involved in altered energy metabolism, such as the glucose transporters GLUT1 and GLUT3, and hexokinases 1 and 2 (Forsythe et al., "Activation of Vascular Endothelial Growth Factor Gene Transcription by Hypoxia-inducible Factor 1," Mol. Cell. Biol. 16:4604-13 (1996); Okino et al., "Hypoxia-inducible Mammalian Gene Expression Analyzed in Vivo at a TATA-driven Promoter and at an Initiator-driven Promoter," J. Biol. Chem. 273:23837-43 (1998)); and (iii) interaction of promoter-bound HIF-1α/1β with coactivator protein p300 (or the homologous CREB binding protein, CBP) leading to upregulation of transcription.

The interaction between the cysteine-histidine rich 1 domain ("CH1") of p300/CBP and the C-terminal transactivation domain ("C-TAD$_{786-826}$") of HIF-1α (Freedman et al., "Structural Basis for Recruitment of CBP/p300 by Hypoxia-inducible Factor-1α," Proc. Nat'l Acad. Sci. USA 99:5367-72 (2002); Dames et al., "Structural Basis for Hif-1α/CBP Recognition in the Cellular Hypoxic Response," Proc. Nat'l Acad. Sci. USA 99:5271-6 (2002)) mediates transactivation of hypoxia-inducible genes (Hirota & Semenza, "Regulation of Angiogenesis by Hypoxia-inducible Factor 1," Crit. Rev. Oncol. Hematol. 59:15-26 (2006); Semenza, "Targeting HIF-1 for Cancer Therapy," Nat. Rev. Cancer 3:721-32 (2003)) (see FIG. 2A). As illustrated in FIGS. 2A-C, structural studies provide a molecular basis for this transcription factor-coactivator interaction and identify two short α-helical domains from HIF-1α as key determinants for its recognition by p300 (Freedman et al., "Structural Basis for Recruitment of CBP/p300 by Hypoxia-Inducible Factor-1α," Proc. Nat'l Acad. Sci. USA 99:5367-72 (2002); Dames et al., "Structural Basis for Hif-1α/CBP Recognition in the Cellular Hypoxic Response," Proc. Nat'l Acad. Sci. USA. 99:5271-76 (2002)). Synthetic mimics of these domains could inhibit HIF-1α/p300 or HIF-1α/CBP complex formation and regulate transcription. Key residues contributing to the binding of one of the two helices (PDB code IL8C, residues 139-147) are shown in FIG. 2C.

Because interaction of HIF-1α C-TAD with transcriptional coactivator p300/CBP is a point of significant amplification in transcriptional response, its disruption with designed protein ligands could be an effective means of suppressing aerobic glycolysis and angiogenesis (i.e., the formation of new blood vessels) in cancers (Hirota & Semenza, "Regulation of Angiogenesis by Hypoxia-inducible Factor 1," Crit. Rev. Oncol. Hematol. 59:15-26 (2006); Ramanathan et al., "Perturbational Profiling of a Cell-line Model of Tumorigenesis by Using Metabolic Measurements," Proc. Nat'l Acad. Sci. USA 102:5992-7 (2005); Underiner et al., "Development of Vascular Endothelial Growth Factor Receptor (VEGFR) Kinase Inhibitors as Anti-angiogenic Agents in Cancer Therapy," Curr. Med. Chem. 11:731-45 (2004)). Although the contact surface of the HIF-1α C-TAD with p300/CBP is extensive (3393 Å$^2$), the inhibition of this protein—protein interaction may not require direct interference. Instead, the induction of a structural change to one of the binding partners (p300/CBP) may be sufficient to disrupt the complex (Kung et al., "Small Molecule Blockade of Transcriptional Coactivation of the Hypoxia-inducible Factor Pathway," *Cancer Cell* 6:33-43 (2004)).

Although inhibition of nuclear protein—protein interactions with small molecules in the past has proven to be difficult (Arkin & Wells, "Small-molecule Inhibitors of Protein—Protein Interactions: Progressing Towards the Dream," *Nat. Rev. Drug Discov.* 3:301-17 (2004)), screens for high-affinity protein ligands have resulted in several remarkable accomplishments (Kung et al., "Small Molecule Blockade of Transcriptional Coactivation of the Hypoxia-inducible Factor Pathway," *Cancer Cell* 6:33-43 (2004); Issaeva et al., "Small Molecule RITA Binds to p53, Blocks p53-HDM-2 Interaction and Activates p53 Function in Tumors," *Nat. Med.* 10:1321-8 (2004); Lepourcelet et al., "Small-molecule Antagonists of the Oncogenic Tcf/β-Catenin Protein Complex," *Cancer Cell* 5:91-102 (2004); Vassilev et al., "In Vivo Activation of the p53 Pathway by Small-molecule Antagonists of MDM2," *Science* 303:844-8 (2004); Grasberger et al., "Discovery and Cocrystal Structure of Benzodiazepinedione HDM2 Antagonists That Activate p53 in Cells," *J. Med. Chem.* 48:909-12 (2005); Ding et al., "Structure-based Design of Potent Non-peptide MDM2 Inhibitors,"*J. Am. Chem. Soc.* 127:10130-1 (2005); Berg et al., "Small-molecule Antagonists of Myc/Max Dimerization Inhibit Myc-induced Transformation of Chicken Embryo Fibroblasts,"*Proc. Nat'l Acad. Sci. USA* 99:3830-5 (2002); International Patent Publication No. WO 2006/066775 to De Munari et al.). Two small molecules, chaetocin 1 (Hauser et al., "Isolation and Structure Elucidation of Chaetocin," *Helv. Chim. Acta* 53(5):1061-73 (1970)) and chetomin 2 (Waksman & Bugie, "Chaetomin, a New Antibiotic Substance Produced by *Chaetomium* Cochliodes I. Formation and Properties," *J. Bacteriol.* 48:527-30 (1944)), have been shown to inhibit the interaction between HIF-1α C-TAD and p300/CBP and to attenuate hypoxia-inducible transcription. Despite the initial encouraging reports, further design of inhibitors of the HIF-1 pathway is needed, because both 1 and 2 have induced coagulative necrosis, anemia, and leukocytosis in experimental animals. It would be desirable to identify other inhibitors of the HIF-1 pathway that lack or have diminished side effects.

The present invention is directed to overcoming these and other deficiencies in the art.

SUMMARY OF THE INVENTION

One aspect of the present invention relates to an oligooxopiperazine of Formula I that mimics helix αB of the C-terminal transactivation domain of HIF-1α:

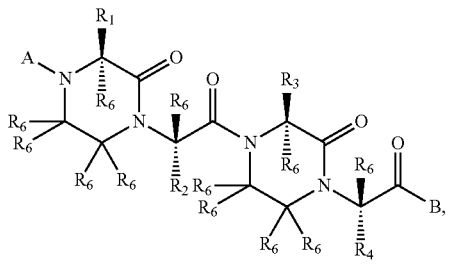

I wherein:
each of $R_1$, $R_2$, $R_3$, and $R_4$ is independently an amino acid side chain, H, $N(R)_2$, OR, halogen, an alkyl, or an aryl; wherein each R is independently H, an alkyl, or an aryl;
each $R_6$ is independently H, $N(R)_2$, OR, halogen, an alkyl, or an aryl; wherein each R is independently H, an alkyl, or an aryl;
A is $X_1$ or C, wherein:
  $X_1$ is H, COR', $CO_2R'$, CONR', an alkyl, an aryl, an arylalkyl, a cycloalkyl, a heteroaryl, a protecting group for protection of an amine, a targeting moiety, or a tag; wherein R' is H, an alkyl, an aryl, an arylalkyl, a cycloalkyl, a heteroaryl, a targeting moiety, or a tag; and
  C is a moiety of the formula

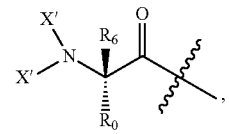

wherein:
  each X' is independently H, COR', $CO_2R'$, CONR', $N(R'')_2$, an alkyl, an aryl, an arylalkyl, a cycloalkyl, a heteroaryl, a targeting moiety, or a tag; wherein:
    R' is H, an alkyl, an aryl, an arylalkyl, a cycloalkyl, a heteroaryl, a targeting moiety, or a tag; and
    each R'' is independently H, an alkyl, an aryl, an arylalkyl, a cycloalkyl, a heteroaryl, a targeting moiety, or a tag;
  $R_0$ is an amino acid side chain, H, $N(R)_2$, OR, halogen, an alkyl, or an aryl; wherein each R is independently H, an alkyl, or an aryl; and
  $R_6$ is H, $N(R)_2$, OR, halogen, an alkyl, or an aryl; wherein each R is independently H, an alkyl, or an aryl; and
B is OR', COR', $N(R''')_2$, an alkyl, an aryl, an arylalkyl, a cycloalkyl, a heteroaryl, a protecting group for protection of a carboxylic acid, a targeting moiety, or a tag; wherein:
  R' is H, an alkyl, an aryl, an arylalkyl, a cycloalkyl, a heteroaryl, a targeting moiety, or a tag; and
  each R''' is independently H, $CO_2R'$, CONR', an alkyl, an aryl, an arylalkyl, a cycloalkyl, a heteroaryl, a targeting moiety, or a tag;
wherein $R_1$ and $R_2$ are hydrophobic and $R_4$ is a hydrogen bond acceptor or hydrogen bond donor or A is a moiety of formula

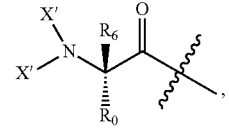

$R_0$ and $R_3$ are hydrophobic, and $R_4$ is a hydrogen bond acceptor or hydrogen bond donor; and
with the proviso that at least one of the following conditions is not met: $R_1$ is a leucine side chain, $R_2$ is a leucine side chain, and $R_4$ is a glutamine side chain.

The present invention is further directed to pharmaceutical formulations containing the oligooxopiperazine of Formula I.

A second aspect of the present invention relates to a method of reducing transcription of a gene in a cell, where transcription of the gene is mediated by interaction of HIF-1α with CREB-binding protein and/or p300. This method involves contacting the cell with an oligooxopiperazine of the present invention under conditions effective to reduce transcription of the gene.

A third aspect of the present invention relates to a method of treating or preventing in a subject a disorder mediated by interaction of HIF-1α with CREB-binding protein and/or p300. This method involves administering an oligooxopiperazine of the present invention to the subject under conditions effective to treat or prevent the disorder.

A fourth aspect of the present invention relates to a method of reducing or preventing angiogenesis in a tissue. This method involves contacting the tissue with an oligooxopiperazine of the present invention under conditions effective to reduce or prevent angiogenesis in the tissue.

A fifth aspect of the present invention relates to a method of inducing apoptosis of a cell. This method involves contacting the cell with an oligooxopiperazine of the present invention under conditions effective to induce apoptosis of the cell.

A sixth aspect of the present invention relates to a method of decreasing survival and/or proliferation of a cell. This method involves contacting the cell with an oligooxopiperazine of the present invention under conditions effective to decrease survival and/or proliferation of the cell.

BRIEF DESCRIPTION OF THE DRAWINGS

FIGS. 2A-C relate to the HIF-1α/TAZ1 structure (Dames et al. *Proc. Nat'l Acad. Sci.* 99:5271 (2002)). FIG. 2A is a schematic diagram illustrating the structure of the complex of the C-terminal transactivation domain ("C-TAD") of HIF-1α with cysteine-histidine rich 1 domain ("CH1") of the coactivator protein p300. The human HIF-1α C-TAD sequence (SEQ ID NO: 1) is shown in FIG. 2B, along with the location of the αA helix (PDB residues 121-127) and αB helix (PDB residues 139-147). FIG. 2C is a table showing the key residues contributing to the binding of helix αB.

DETAILED DESCRIPTION OF THE INVENTION

Figure 1:
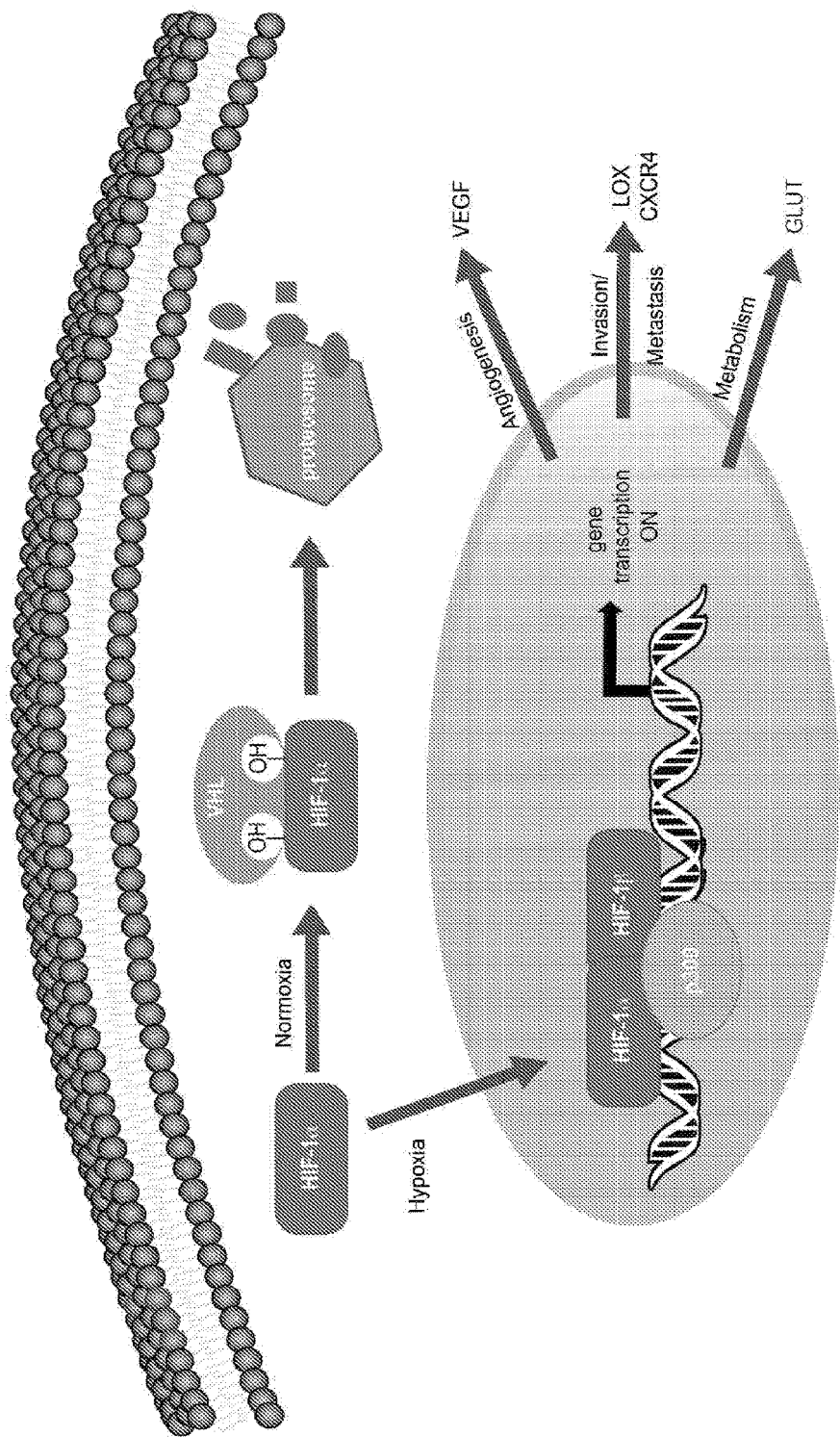
FIG. 1 is a schematic illustration of HIF-1α-mediated regulation of oxygen-dependent transcription (Rankin & Giaccia, *Cell Death Different.* 15:678 (2008)).
Figure 3:
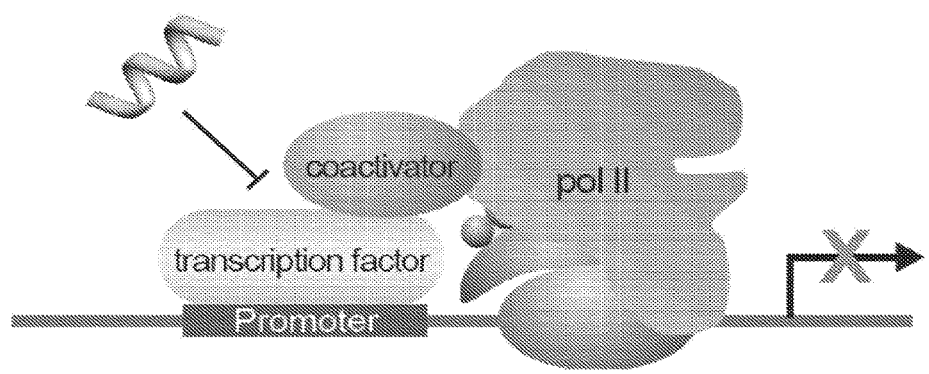
FIG. 3 is a schematic diagram illustrating the interaction between transcription factors, coactivators, and promoters in initiating transcription (Guarracino et al., *Biopolymers* 95:1 (2011)).

Described herein is the design of oligooxopiperazine helix mimetics that inhibit transcription of hypoxia inducible genes by modulating the interaction between HIF-1α transcription factor and coactivator p300/CBP. As illustrated in FIG. 3, transcription factors are involved in an intricate web of interactions with partner proteins and promoter DNA, which result in recruitment of chromatin-remodeling enzymes and assembly of the preinitiation complex (MARK PTASHNE & ALEXANDER GANN, GENES AND SIGNALS (2002), which is hereby incorporated by reference in its entirety). Because of the essential role gene expression plays in the progression of diseases, synthetic agents that modulate transcription in a defined manner are attractive candidates for drug design (Arndt, "Small Molecule Modulators of Transcription,"*Angew Chem. Int'l Ed. Engl.* 45:4552-60 (2006); Berg, "Inhibition of Transcription Factors with Small Organic Molecules," *Curr. Opin. Chem. Biol.* 12:464-71 (2008); Mapp, "Regulating Transcription: A Chemical Perspective," *Org. Biomol. Chem.* 1:2217-20 (2003), each of which is hereby incorporated by reference in its entirety).

A first aspect of the present invention relates to an oligooxopiperazine of Formula I that mimics helix αB of the C-terminal transactivation domain of HIF-1α:

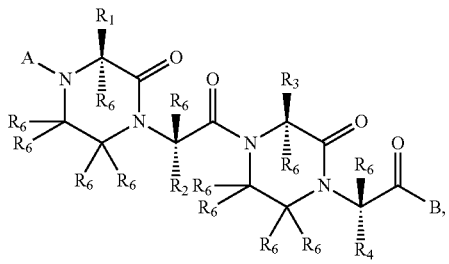

I wherein:
each of $R_1$, $R_2$, $R_3$, and $R_4$ is independently an amino acid side chain, H, $N(R)_2$, OR, halogen, an alkyl, or an aryl; wherein each R is independently H, an alkyl, or an aryl;
each $R_6$ is independently H, $N(R)_2$, OR, halogen, an alkyl, or an aryl; wherein each R is independently H, an alkyl, or an aryl;
A is $X_1$ or C, wherein:
  $X_1$ is H, COR', $CO_2R'$, CONR', an alkyl, an aryl, an arylalkyl, a cycloalkyl, a heteroaryl, a protecting group for protection of an amine, a targeting moiety, or a tag; wherein R' is H, an alkyl, an aryl, an arylalkyl, a cycloalkyl, a heteroaryl, a targeting moiety, or a tag; and
  C is a moiety of the formula

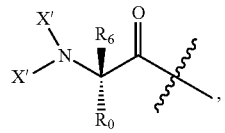

wherein:
  each X' is independently H, COR', $CO_2R'$, CONR', $N(R'')_2$, an alkyl, an aryl, an arylalkyl, a cycloalkyl, a heteroaryl, a targeting moiety, or a tag; wherein:
    R' is H, an alkyl, an aryl, an arylalkyl, a cycloalkyl, a heteroaryl, a targeting moiety, or a tag; and
    each R'' is independently H, an alkyl, an aryl, an arylalkyl, a cycloalkyl, a heteroaryl, a targeting moiety, or a tag;
  $R_0$ is an amino acid side chain, H, $N(R)_2$, OR, halogen, an alkyl, or an aryl; wherein each R is independently H, an alkyl, or an aryl; and
  $R_6$ is H, $N(R)_2$, OR, halogen, an alkyl, or an aryl; wherein each R is independently H, an alkyl, or an aryl; and
B is OR', COR', $N(R''')_2$, an alkyl, an aryl, an arylalkyl, a cycloalkyl, a heteroaryl, a protecting group for protection of a carboxylic acid, a targeting moiety, or a tag; wherein:
  R' is H, an alkyl, an aryl, an arylalkyl, a cycloalkyl, a heteroaryl, a targeting moiety, or a tag; and
  each R''' is independently H, $CO_2R'$, CONR', an alkyl, an aryl, an arylalkyl, a cycloalkyl, a heteroaryl, a targeting moiety, or a tag;
wherein $R_1$ and $R_2$ are hydrophobic and $R_4$ is a hydrogen bond acceptor or hydrogen bond donor or A is a moiety of formula

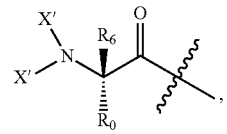

$R_0$ and $R_3$ are hydrophobic, and $R_4$ is a hydrogen bond acceptor or hydrogen bond donor; and
with the proviso that at least one of the following conditions is not met: $R_1$ is a leucine side chain, $R_2$ is a leucine side chain, and $R_4$ is a glutamine side chain.

Amino acid side chains according to this and all aspects of the present invention can be any amino acid side chain—from natural or nonnatural amino acids—including alpha amino acids, disubstituted amino acids, beta amino acids, gamma amino acids, L-amino acids, D-amino acids, etc.

As used herein, the term "alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

As used herein, "cycloalkyl" refers to a non-aromatic saturated or unsaturated mono- or polycyclic ring system which may contain 3 to 6 carbon atoms, and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, or syn-bicyclopropane.

As used herein, the term "aryl" refers to an aromatic monocyclic or polycyclic ring system containing from 6 to 19 carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "arylalkyl" refers to a radical of the formula $-R^aR^b$ where $R^a$ is an alkyl radical as defined above and $R^b$ is an aryl radical as defined above. The alkyl radical and the cycloalkyl radical may be optionally substituted as defined above.

As used herein, "heteroaryl" refers to an aromatic ring radical which consists of carbon atoms and from one to five heteroatoms selected from the group consisting of nitrogen, oxygen, and sulfur. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuryl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl. Additional heteroaryls are described in COMPREHENSIVE HETEROCYCLIC CHEMISTRY: THE STRUCTURE, REACTIONS, SYNTHESIS AND USE OF HETEROCYCLIC COMPOUNDS (Katritzky et al. eds., 1984), which is hereby incorporated by reference in its entirety.

The oligooxopiperazines of Formula I may comprise a protecting group that is suitable for the protection of an amine or a carboxylic acid. Such protecting groups function primarily to protect or mask the reactivity of functional groups. Protecting groups that are suitable for the protection of an amine group are well known in the art, including without limitation, carbamates, amides, N-alkyl and N-aryl amines, imine derivatives, enamine derivatives, and N-hetero atom derivatives as described by THEODORA W. GREENE & PETER G. M. WUTS, PROTECTIVE GROUPS IN ORGANIC SYNTHESIS 494-615 (1999), which is hereby incorporated by reference in its entirety. Protecting groups that are suitable for the protection of a carboxylic acid are also well known in the art. Suitable carboxylic acid protecting groups include, without limitation, esters (e.g., substituted methyl esters, 2-substituted ethyl esters, 2,6-dialkylphenyl esters, substituted benzyl esters, silyl esters, and stannyl esters), amides, and hydrazides as described by THEODORA W. GREENE & PETER G. M. WUTS, PROTECTIVE GROUPS IN ORGANIC SYNTHESIS 372-450 (1999), which is hereby incorporated by reference in its entirety. Methods of protecting and deprotecting amine and carboxylic acids vary depending on the chosen protecting group; however, these methods are well known in the art and described in THEODORA W. GREENE & PETER G. M. WUTS, PROTECTIVE GROUPS IN ORGANIC SYNTHESIS 372-450 and 494-615 (1999), which is hereby incorporated by reference in its entirety.

A targeting moiety according to the present invention functions to (i) promote the cellular uptake of the oligooxopiperazine, (ii) target the oligooxopiperazine to a particular cell or tissue type (e.g., signaling peptide sequence), or (iii) target the oligooxopiperazine to a specific sub-cellular localization after cellular uptake (e.g., transport peptide sequence).

To promote the cellular uptake of an oligooxopiperazine of the present invention, the targeting moiety may be a cell penetrating peptide (CPP). CPPs translocate across the plasma membrane of eukaryotic cells by a seemingly energy-independent pathway and have been used successfully for intracellular delivery of macromolecules, including antibodies, peptides, proteins, and nucleic acids, with molecular weights several times greater than their own. Several commonly used CPPs, including polyarginines, transportant, protamine, maurocalcine, and M918, are suitable targeting moieties for use in the present invention and are well known in the art (see Stewart et al., "Cell-Penetrating Peptides as Delivery Vehicles for Biology and Medicine," *Organic Biomolecular Chem.* 6:2242-2255 (2008), which is hereby incorporated by reference in its entirety).

Additionally, methods of making CPP are described in U.S. Patent Application Publication No. 20080234183 to Hallbrink et al., which is hereby incorporated by reference in its entirety.

Another suitable targeting moiety useful for enhancing the cellular uptake of the oligooxopiperazine is an "importation competent" signal peptide as disclosed by U.S. Pat. No. 6,043,339 to Lin et al., which is hereby incorporated by reference in its entirety. An importation competent signal peptides is generally about 10 to about 50 amino acid residues in length, typically hydrophobic residues, that render the oligooxopiperazine capable of penetrating through the cell membrane from outside the cell to the interior of the cell. An exemplary importation competent signal peptide includes the signal peptide from Kaposi fibroblast growth factor (see U.S. Pat. No. 6,043,339 to Lin et al., which is hereby incorporated by reference in its entirety). Other suitable peptide sequences can be selected from the SIGPEP database (see von Heijne G., "SIGPEP: A Sequence Database for Secretory Signal Peptides," *Protein Seq. Data Anal.* 1(1):41-42 (1987), which is hereby incorporated by reference in its entirety).

Another suitable targeting moiety is a signal peptide sequence capable of targeting the oligooxopiperazine to a particular tissue or cell type. The signaling peptide can include at least a portion of a ligand binding protein. Suitable ligand binding proteins include high-affinity antibody fragments (e.g., Fab, Fab' and F(ab')$_2$), single-chain Fv antibody fragments), nanobodies or nanobody fragments, fluorobodies, or aptamers. Other ligand binding proteins include biotin-binding proteins, lipid-binding proteins, periplasmic binding proteins, lectins, serum albumins, enzymes, phosphate and sulfate binding proteins, immunophilins, metallothionein, or various other receptor proteins. For cell specific targeting, the signaling peptide is preferably a ligand binding domain of a cell specific membrane receptor. Thus, when the modified oligooxopiperazine is delivered intravenously or otherwise introduced into blood or lymph, the oligooxopiperazine will adsorb to the targeted cell, and the targeted cell will internalize the oligooxopiperazine. For example, if the target cell is a cancer cell, the oligooxopiperazine may be conjugated to an anti-C3B(I) antibody as disclosed by U.S. Pat. No. 6,572,856 to Taylor et al., which is hereby incorporated by reference in its entirety. Alternatively, the oligooxopiperazine may be conjugated to an alphafeto protein receptor as disclosed by U.S. Pat. No. 6,514,685 to Moro, or to a monoclonal GAH antibody as disclosed by U.S. Pat. No. 5,837,845 to Hosokawa, which are hereby incorporated by reference in their entirety. For targeting an oligooxopiperazine to a cardiac cell, the oligooxopiperazine may be conjugated to an antibody recognizing elastin microfibril interfacer (EMILIN2) (Van Hoof et al., "Identification of Cell Surface for Antibody-Based Selection of Human Embryonic Stem Cell-Derived Cardiomyocytes," *J Proteom Res* 9:1610-18 (2010), which is hereby incorporated by reference in its entirety), cardiac troponin I, connexin-43, or any cardiac cell-surface membrane receptor that is known in the art. For targeting an oligooxopiperazine to a hepatic cell, the signaling peptide may include a ligand domain specific to the hepatocyte-specific asialoglycoprotein receptor. Such chimeric oligooxopiperazines can be prepared using similar methods as those for preparing chimeric proteins and peptides described in U.S. Pat. No. 5,817,789 to Heartlein et al., which is hereby incorporated by reference in its entirety.

Another suitable targeting moiety is a transport peptide that directs intracellular compartmentalization of the oligooxopiperazine once it is internalized by a target cell or tissue. For example, if the protein activity or protein—protein interaction that is sought to be inhibited occurs in the endoplasmic reticulum (ER), the oligooxopiperazine can be conjugated to an ER transport peptide sequence. A number of such signal peptides are known in the art, including the signal peptide MMSFVSLLLVGILFYATEAEQLT-KCEVFQ (SEQ ID NO: 3). Other suitable ER signal peptides include the N-terminus endoplasmic reticulum targeting sequence of the enzyme 17β-hydroxysteroid dehydrogenase type 11 (Horiguchi et al., "Identification and Characterization of the ER/Lipid Droplet-Targeting Sequence in 17β-hydroxysteroid Dehydrogenase Type 11," *Arch. Biochem. Biophys.* 479(2):121-30 (2008), which is hereby incorporated by reference in its entirety), or any of the ER signaling peptides (including the nucleic acid sequences encoding the ER signal peptides) disclosed in U.S. Patent Publication No. 20080250515 to Reed et al., which is hereby incorporated by reference in its entirety. Additionally, the oligooxopiperazine of the present invention can contain an ER retention signal, such as the retention signal KEDL (SEQ ID NO: 4). Methods of modifying the oligooxopiperazines of the present invention to incorporate transport peptides for localization of the oligomers to the ER can be carried out as described in U.S. Patent Publication No. 20080250515 to Reed et al., which is hereby incorporated by reference in its entirety.

If the protein activity or protein—protein interaction that is sought to be inhibited occurs in the nucleus, the oligooxopiperazine can include a nuclear localization transport signal. Suitable nuclear transport peptide sequences are known in the art, including the nuclear transport peptide PPKKKRKV (SEQ ID NO: 5). Other nuclear localization transport signals include, for example, the nuclear localization sequence of acidic fibroblast growth factor and the nuclear localization sequence of the transcription factor NF-KB p50 as disclosed by U.S. Pat. No. 6,043,339 to Lin et al., which is hereby incorporated by reference in its entirety. Other nuclear localization peptide sequences known in the art are also suitable for use in the accordance with this aspect of the invention.

Suitable transport peptide sequences for targeting to the mitochondria include MLSLRQSIRFFKPATRTLCSSRYLL (SEQ ID NO: 6). Other suitable transport peptide sequences suitable for selectively targeting the oligooxopiperazine of the present invention to the mitochondria are disclosed in U.S. Published Patent Application No. 20070161544 to Wipf, which is hereby incorporated by reference in its entirety.

A "tag" as used herein includes any labeling moiety that facilitates the detection, quantitation, separation, and/or purification of the oligooxopiperazine of the present invention. Suitable tags include purification tags, radioactive or fluorescent labels, and enzymatic tags.

Purification tags, such as poly-histidine ($His_{6-}$), a glutathione-S-transferase (GST-), or maltose-binding protein (MBP-), can assist in oligomer purification or separation but can later be removed, i.e., cleaved from the oligooxopiperazine following recovery. Protease-specific cleavage sites can be used to facilitate the removal of the purification tag. The desired oligooxopiperazine product can be purified further to remove the cleaved purification tags.

Other suitable tags include radioactive labels, such as, $^{125}I$, $^{131}I$, $^{111}In$, or $^{99}TC$. Methods of radiolabeling compounds, are known in the art and described in U.S. Pat. No. 5,830,431 to Srinivasan et al., which is hereby incorporated by reference in its entirety. Radioactivity is detected and quantified using a scintillation counter or autoradiography.

Alternatively, the oligooxopiperazine can be conjugated to a fluorescent tag. Suitable fluorescent tags include, without limitation, chelates (europium chelates), fluorescein and its derivatives, rhodamine and its derivatives, dansyl, Lissamine, phycoerythrin and Texas Red. The fluorescent labels can be conjugated to the oligooxopiperazine using techniques disclosed in CURRENT PROTOCOLS IN IMMUNOLOGY (Coligen et al. eds., 1991), which is hereby incorporated by reference in its entirety. Fluorescence can be detected and quantified using a fluorometer.

Enzymatic tags generally catalyze a chemical alteration of a chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Examples of suitable enzymatic tags include luciferases (e.g., firefly luciferase and bacterial luciferase; see e.g., U.S. Pat. No. 4,737,456 to Weng et al., which is hereby incorporated by reference in its entirety), luciferin, 2,3-dihydrophthalazinediones, malate dehydrogenase, urease, peroxidases (e.g., horseradish peroxidase), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (e.g., uricase and xanthine oxidase), lactoperoxidase, microperoxidase, and the like. Techniques for conjugating enzymes to proteins and peptides are described in O'Sullivan et al., *Methods for the Preparation of Enzyme Antibody Conjugates for Use in Enzyme Immunoassay*, in METHODS IN ENZYMOLOGY 147-66 (Langone et al. eds., 1981), which is hereby incorporated by reference in its entirety, can be used for conjugating enzymes to oligooxopiperazines of the present invention. Such tags may be particularly useful for detecting inhibition of protein—protein interactions using the oligooxopiperazine of the present invention.

The oligooxopiperazines of Formula I also comprise a hydrogen bond donor or hydrogen bond acceptor. Hydrogen bond acceptors contain an atom with an electron lone-pair to interact with a proton on an electronegative atom. Suitable examples include, without limitation, carbonyl groups and aromatic amines such as pyridine and imidazole. Hydrogen bond donors contain an electronegative atom with at least one proton to share. Suitable examples include, without limitation, amine, amide, carboxylic acids, hydroxyl, and thiol functional groups.

Exemplary oligooxopiperazine compounds of Formula I include, without limitation BB2-125, BB2-162, and BB2-164.

Peptides of the present invention may be made using methods in the art. Suitable methods include those described in U.S. patent application Ser. No. 12/917,176, which is hereby incorporated by reference in its entirety.

Also encompassed by the present invention is a pharmaceutical formulation that includes an oligooxopiperazine of the present invention and a pharmaceutically acceptable vehicle.

Suitable pharmaceutical formulations include the oligooxopiperazine and any pharmaceutically acceptable adjuvants, carriers, solutions, suspensions, emulsions, excipients, powders, and/or stabilizers, and can be in solid or liquid form, such as tablets, capsules, powders, solutions, suspensions, or emulsions. The compositions preferably contain from about 0.01 to about 99 weight percent, more preferably from about 2 to about 60 weight percent, of the oligooxopiperazine together with the adjuvants, carriers and/or excipients. The amount of active compound in such therapeutically useful compositions is such that a suitable dosage unit will be obtained.

In addition, the pharmaceutical formulations of the present invention may further comprise one or more pharmaceutically acceptable diluents or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

For oral therapeutic administration, the oligooxopiperazines of the invention may be incorporated with excipients and used in the form of tablets, capsules, elixirs, suspensions, syrups, and the like. Such compositions and preparations should contain at least 0.1% of the oligooxopiperazine. The percentage of the oligooxopiperazine in these compositions may, of course, be varied and may conveniently be between about 2% to about 60% of the weight of the unit. The amount of the oligooxopiperazine in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, or alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient(s), sucrose as a sweetening agent, methyl and propylparabens as preservatives, a dye, and flavoring such as cherry or orange flavor.

Solutions or suspensions of the oligooxopiperazine (for example, for parenteral administration) can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycol or polyethylene glycol, are preferred liquid carriers, particularly for injectable solutions. Under ordinary conditions of storage and use, these preparations contain a preservative to prevent the growth of microorganisms.

Pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

A second aspect of the present invention relates to inhibiting the HIF-1α-p300/CBP interaction using the oligooxopiperazines of the present invention.

One embodiment of this aspect of the present invention relates to a method of reducing transcription of a gene in a cell, where transcription of the gene is mediated by interaction of HIF-1α with CREB-binding protein and/or p300. This method involves contacting the cell with an oligooxopiperazine of the present invention under conditions effective to cause nuclear uptake of the oligooxopiperazine, where the oligooxopiperazine disrupts interaction of HIF-1α and p300/CBP and thereby reduces transcription of the gene.

Genes whose transcription is mediated by interaction of HIF-1α with CBP and/or p300 include $\alpha_{1B}$-adrenergic receptor, adenylate kinase 3, adrenomedullin, aldolase A, aldolase C, carbonic anhydrase IX, ceruloplasmin, chemokine receptor type 4 (CXCR4, fusin, CD184), c-Met, endothelin-1, enolase 1, erythropoietin, glucose transporter 1, glucose transporter 3, glyceraldehyde-3-phosphate dehydrogenase, heme oxygenase 1, hexokinase 1, hexokinase 2, IGF binding protein 1, IGF binding protein 3, insulin-like growth factor 2, lactate dehydrogenase A, lysyl oxidase, monoamine oxidase isoform A, monoamine oxidase isoform B, nitric oxide synthase 2, p21, $p35^{srg}$, phosphofructokinase, phosphoglycerate kinase 1, plasminogen activator inhibitor 1, pyruvate kinase M, stromal-derived factor 1, transferrin receptor, transferrin, transforming growth factor $\beta_3$, triose phosphate isomerase 1, vascular endothelial growth factor, vascular endothelial growth factor receptor FLT-1, and vascular endothelial growth factor receptor KDR/Flk-1. Some uses for inhibiting transcription of these genes are shown in Table 1.

TABLE 1

Example Disorders

| Gene | Treat/prevent |
|---|---|
| adrenomedullin | Pheochromocytoma |
| carbonic anhydrase IX | Cancer |
| ceruloplasmin | Lymphoma, acute and chronic inflammation, rheumatoid arthritis |
| chemokine receptor type 4 (CXCR4, fusin, CD184) | Cancer stem cell migration, inflammation |
| c-Met | Metastasis (tumor, incl. cancer) |
| endothelin-1 | Abnormal vasoconstriction |
| enolase 1 | Hashimoto's encephalopathy, severe asthma |

TABLE 1-continued

Example Disorders

| Gene | Treat/prevent |
| --- | --- |
| erythropoietin | Abnormal oxygen transport |
| glucose transporter 1 | Aerobic glycolysis (Warburg effect) |
| glucose transporter 3 | Aerobic glycolysis (Warburg effect) |
| heme oxygenase 1 | Abnormal oxygen transport |
| hexokinase 1 | Aerobic glycolysis (Warburg effect) |
| hexokinase 2 | Aerobic glycolysis (Warburg effect) |
| IGF binding protein 1 | Abnormal development and function of organs (brain, liver) |
| IGF binding protein 3 | Abnormal development and function of organs (brain, liver) |
| insulin-like growth factor 2 | Abnormal development and function of organs (brain, liver) |
| lactate dehydrogenase A | Myocardial infarction |
| lysyl oxidase | Metastasis (tumor, esp. breast cancer) |
| monoamine oxidase isoform A | Aggression, depression, cancer, esp. prostate |
| monoamine oxidase isoform B | Aggression, depression, cancer, esp. prostate |
| nitric oxide synthase 2 | Abnormal vasomotor tone |
| phosphofructokinase | Aerobic glycolysis (Warburg effect) |
| phosphoglycerate kinase 1 | Aerobic glycolysis (Warburg effect) |
| stromal-derived factor 1 | Cancer stem cell migration, inflammation |
| tranferrin receptor | Abnormal iron uptake/metabolism |
| transferrin | Abnormal iron uptake/metabolism |
| triose phosphate isomerase 1 | Aerobic glycolysis (Warburg effect) |
| vascular endothelial growth factor | Angiogenesis (tumor, incl. cancer) |
| vascular endothelial growth factor receptor FLT-1 | Angiogenesis (tumor, incl. cancer) |
| vascular endothelial growth factor receptor KDR/Flk-1 | Angiogenesis (tumor, incl. cancer) |

Another embodiment of this aspect of the present invention relates to a method of treating or preventing in a subject a disorder mediated by interaction of HIF-1α with CBP and/or p300. This method involves administering an oligooxopiperazine of the present invention to the subject under conditions effective to treat or prevent the disorder.

Disorders that can be treated or prevented include, for example, retinal ischemia (Zhu et al., "Long-term Tolerance to Retinal Ischemia by Repetitive Hypoxic Preconditioning: Role of HIF-1α and Heme Oxygenase-1," *Invest. Ophthalmol. Vis. Sci.* 48:1735-43 (2007); Ding et al., "Retinal Disease in Mice Lacking Hypoxia-inducible Transcription Factor-2α," *Invest. Ophthalmol. Vis. Sci.* 46:1010-6 (2005), each of which is hereby incorporated by reference in its entirety), pulmonary hypertension (Simon et al., "Hypoxia-induced Signaling in the Cardiovascular System,"*Annu. Rev. Physiol.* 70:51-71 (2008); Eul et al., "Impact of HIF-1α and HIF-2α on Proliferation and Migration of Human Pulmonary Artery Fibroblasts in Hypoxia,"*FASEB J.* 20:163-5 (2006), each of which is hereby incorporated by reference in its entirety), intrauterine growth retardation (Caramelo et al., "Respuesta a la Hipoxia. Un Mecanismo Sistémico Basado en el Control de la Expresión Génica [Response to Hypoxia. A Systemic Mechanism Based on the Control of Gene Expression]," *Medicina B. Aires* 66:155-64 (2006); Tazuke et al., "Hypoxia Stimulates Insulin-like Growth Factor Binding Protein 1 (IGFBP-1) Gene Expression in HepG2 Cells: A Possible Model for IGFBP-1 Expression in Fetal Hypoxia," *Proc. Nat'l Acad. Sci. USA* 95:10188-93 (1998), each of which is hereby incorporated by reference in its entirety), diabetic retinopathy (Ritter et al., "Myeloid Progenitors Differentiate into Microglia and Promote Vascular Repair in a Model of Ischemic Retinopathy," *J. Clin. Invest.* 116:3266-76 (2006); Wilkinson-Berka et al., "The Role of Growth Hormone, Insulin-like Growth Factor and Somatostatin in Diabetic Retinopathy," *Curr. Med. Chem.* 13:3307-17 (2006); Vinores et al., "Implication of the Hypoxia Response Element of the Vegf Promoter in Mouse Models of Retinal and Choroidal Neovascularization, but Not Retinal Vascular Development," *J. Cell. Physiol.* 206: 749-58 (2006); Caldwell et al., "Vascular Endothelial Growth Factor and Diabetic Retinopathy: Role of Oxidative Stress," Curr. Drug Targets 6:511-24 (2005), each of which is hereby incorporated by reference in its entirety), age-related macular degeneration (Inoue et al., "Expression of Hypoxia-inducible Factor 1α and 2α in Choroidal Neovascular Membranes Associated with Age-related Macular Degeneration," *Br. J Ophthalmol.* 91:1720-1 (2007); Zuluaga et al., "Synergies of VEGF Inhibition and Photodynamic Therapy in the Treatment of Age-related Macular Degeneration," *Invest. Ophthalmol. Vis. Sci.* 48:1767-72 (2007); Provis, "Development of the Primate Retinal Vasculature," *Prog. Retin. Eye Res.* 20:799-821 (2001), each of which is hereby incorporated by reference in its entirety), diabetic macular edema (Vinores et al., "Implication of the Hypoxia Response Element of the Vegf Promoter in Mouse Models of Retinal and Choroidal Neovascularization, but Not Retinal Vascular Development," *J. Cell. Physiol.* 206: 749-58 (2006); Forooghian & Das, "Anti-angiogenic Effects of Ribonucleic Acid Interference Targeting Vascular Endothelial Growth Factor and Hypoxia-inducible Factor-1α," *Am. J. Ophthalmol.* 144:761-8 (2007), each of which is hereby incorporated by reference in its entirety), and cancer (Marignol et al., "Hypoxia in Prostate Cancer: A Powerful Shield Against Tumour Destruction?" *Cancer Treat. Rev.* 34:313-27 (2008); Galanis et al., "Reactive Oxygen Species and HIF-1 Signalling in Cancer," *Cancer Lett.* 266:12-20 (2008); Ushio-Fukai & Nakamura, "Reactive Oxygen Species and Angiogenesis: NADPH Oxidase as Target for Cancer Therapy," *Cancer Lett.* 266:37-52 (2008); Adamski et al., "The Cellular Adaptations to Hypoxia as Novel Therapeutic Targets in Childhood Cancer," *Cancer Treat. Rev.* 34:231-46 (2008); Toffoli & Michiels, "Intermittent Hypoxia Is a Key Regulator of Cancer Cell and Endothelial Cell Interplay in Tumours," *FEBS J.* 275:2991-3002 (2008); Peehl & Coram, "The Significance of Monoamine Oxidase-A Expression in High Grade Prostate Cancer," *J. Urol.* 180:2206-11 (2008); Flamand & Zhao, "Targeting Monoamine Oxidase A in Advanced Prostate Cancer," *J. Cancer Res. Clin. Oncol.* 136:1761-71 (2010), each of which is hereby incorporated by reference in its entirety).

Yet another embodiment of this aspect of the present invention relates to a method of reducing or preventing angiogenesis in a tissue. This method involves contacting the tissue with an oligooxopiperazine of the present invention under conditions effective to reduce or prevent angiogenesis in the tissue.

Another embodiment of this aspect of the present invention relates to a method of inducing apoptosis of a cell. This method involves contacting the cell with an oligooxopiperazine of the present invention under conditions effective to induce apoptosis of the cell.

Another embodiment of this aspect of the present invention relates to a method of decreasing survival and/or proliferation of a cell. This method involves contacting the cell with an oligooxopiperazine of the present invention under conditions effective to decrease survival and/or proliferation of the cell.

Contacting (including administering) according to this aspect of the present invention can be carried out using methods that will be apparent to the skilled artisan, and can be done in vitro or in vivo.

One approach for delivering agents into cells involves the use of liposomes. Basically, this involves providing a liposome which includes agent(s) to be delivered, and then contacting the target cell, tissue, or organ with the liposomes under conditions effective for delivery of the agent into the cell, tissue, or organ.

This liposome delivery system can also be made to accumulate at a target organ, tissue, or cell via active targeting (e.g., by incorporating an antibody or hormone on the surface of the liposomal vehicle). This can be achieved according to known methods.

An alternative approach for delivery of protein- or polypeptide-containing agents (e.g., oligooxopiperazines of the present invention containing one or more protein or polypeptide side chains) involves the conjugation of the desired agent to a polymer that is stabilized to avoid enzymatic degradation of the conjugated protein or polypeptide. Conjugated proteins or polypeptides of this type are described in U.S. Pat. No. 5,681,811 to Ekwuribe, which is hereby incorporated by reference in its entirety.

Yet another approach for delivery of agents involves preparation of chimeric agents according to U.S. Pat. No. 5,817,789 to Heartlein et al., which is hereby incorporated by reference in its entirety. The chimeric agent can include a ligand domain and the agent (e.g., an oligooxopiperazine of the invention). The ligand domain is specific for receptors located on a target cell. Thus, when the chimeric agent is delivered intravenously or otherwise introduced into blood or lymph, the chimeric agent will adsorb to the targeted cell, and the targeted cell will internalize the chimeric agent.

Oligooxopiperazines of the present invention may be delivered directly to the targeted cell/tissue/organ.

Additionally and/or alternatively, the oligooxopiperazines may be administered to a non-targeted area along with one or more agents that facilitate migration of the oligooxopiperazines to (and/or uptake by) a targeted tissue, organ, or cell. As will be apparent to one of ordinary skill in the art, the oligooxopiperazine itself can be modified to facilitate its transport to a target tissue, organ, or cell, including its transport across the blood-brain barrier; and/or to facilitate its uptake by a target cell (e.g., its transport across cell membranes). In a preferred embodiment, the oligooxopiperazine of the invention is modified, and/or delivered with an appropriate vehicle, to facilitate its delivery to the nucleus of the target cell (Wender et al., "The Design, Synthesis, and Evaluation of Molecules That Enable or Enhance Cellular Uptake: Peptoid Molecular Transporters," *Proc. Nat'l Acad. Sci. USA* 97:13003-8 (2000); Roberts, "Buyer's Guide to Protein Transduction Reagents," *Scientist* 18:42-3 (2004); Joliot & Prochiantz, "Transduction Peptides: From Technology to Physiology," *Nat. Cell Biol.* 6:189-96 (2004), each of which is hereby incorporated by reference in its entirety). Some example target cells, tissues, and/or organs for the embodiments described above are shown in Table 2.

TABLE 2

Example Target Cells/Tissues/Organs

| Desired Effect | Example Target(s) |
| --- | --- |
| Inhibit transcription of: | |
| adrenomedullin | Pheochromocytoma |
| carbonic anhydrase IX | Tumor cells/tissue, incl. cancer |
| ceruloplasmin | Lymphocytes/lymphatic tissue, inflamed tissue, rheumatoid arthritic tissue |
| chemokine receptor type 4 (CXCR4, fusin, CD184) | Tumor cells/tissue, incl. cancer |
| c-Met | Tumor cells/tissue, incl. cancer |
| endothelin-1 | Endothelium |
| enolase 1 | Liver, brain, kidney, spleen, adipose, lung |
| erythropoietin | Liver, kidney |
| glucose transporter 1 | Tumor, incl. cancer |
| glucose transporter 3 | Tumor, incl. cancer |
| hexokinase 1 | Tumor, incl. cancer |
| hexokinase 2 | Tumor, incl. cancer |
| IGF binding protein 1 | Brain, liver |
| IGF binding protein 3 | Brain, liver |
| insulin-like growth factor 2 | Brain, liver |
| lactate dehydrogenase A | Heart |
| lysyl oxidase | Tumor cells/tissue, incl. cancer |
| monoamine oxidase isoform A | Tumor cells/tissue, esp. prostate cancer |
| monoamine oxidase isoform B | Tumor cells/tissue, esp. prostate cancer |
| nitric oxide synthase 2 | Vessels, cardiovascular cells/tissue |
| phosphofructokinase | Tumor, incl. cancer |
| phosphoglycerate kinase 1 | Tumor, incl. cancer |
| stromal-derived factor 1 | Tumor cells/tissue, incl. cancer |
| transferrin | Liver |
| triose phosphate isomerase 1 | Tumor, incl. cancer |
| vascular endothelial growth factor (VEGF) | Tumor cells/tissue, incl. cancer |
| VEGF receptor FLT-1 | Tumor cells/tissue, incl. cancer |
| VEGF receptor KDR/Flk-1 | Tumor cells/tissue, incl. cancer |
| Treat or prevent: | |
| retinal ischemia | Retina (eye) |
| pulmonary hypertension | Lungs |
| intrauterine growth retardation | Uterus |
| diabetic retinopathy | Retina (eye) |
| age-related macular degeneration | Retina (eye) |
| diabetic macular edema | Retina (eye) |
| Reduce or prevent angiogenesis | Tumor cells/tissue, incl. cancer |
| Reduce or prevent metastasis | Tumor cells/tissue, incl. cancer |
| Decrease cell survival and/or proliferation | Cancerous cells, cells contained in the endothelial vasculature of a tissue that contains cancerous cells |

In vivo administration can be accomplished either via systemic administration to the subject or via targeted administration to affected tissues, organs, and/or cells, as described above. Typically, the therapeutic agent (i.e., an oligooxopiperazine of the present invention) will be administered to a patient in a vehicle that delivers the therapeutic agent(s) to the target cell, tissue, or organ. Typically, the therapeutic agent will be administered as a pharmaceutical formulation, such as those described above.

Exemplary routes of administration include, without limitation, orally, topically, transdermally, parenterally, subcutaneously, intravenously, intramuscularly, intraperitoneally, intraventricularly, and intralesionally; by intratracheal inoculation, aspiration, airway instillation, aerosolization, nebulization, intranasal instillation, oral or nasogastric instillation, intraperitoneal injection, intravascular injection, intravenous injection, intra-arterial injection (such as via the pulmonary artery), intramuscular injection, and intrapleural instillation; by application to mucous membranes (such as that of the nose, throat, bronchial tubes, genitals, and/or anus); and by implantation of a sustained release vehicle.

For use as aerosols, an oligooxopiperazine of the present invention in solution or suspension may be packaged in a pressurized aerosol container together with suitable propellants, for example, hydrocarbon propellants like propane, butane, or isobutane with conventional adjuvants. The oligooxopiperazines of the present invention also may be administered in a non-pressurized form.

Exemplary delivery devices include, without limitation, nebulizers, atomizers, liposomes (including both active and passive drug delivery techniques) (Wang & Huang, "pH-Sensitive Immunoliposomes Mediate Target-cell-specific Delivery and Controlled Expression of a Foreign Gene in Mouse," *Proc. Nat'l Acad. Sci. USA* 84:7851-5 (1987); Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al.; Wolff et al., "The Use of Monoclonal Anti-Thy1 IgG1 for the Targeting of Liposomes to AKR-A Cells in Vitro and in Vivo," *Biochim. Biophys. Acta* 802:259-73 (1984), each of which is hereby incorporated by reference in its entirety), transdermal patches, implants, implantable or injectable protein depot compositions, and syringes. Other delivery systems which are known to those of skill in the art can also be employed to achieve the desired delivery of the oligooxopiperazine to the desired organ, tissue, or cells in vivo to effect this aspect of the present invention.

Contacting (including in vivo administration) can be carried out as frequently as required and for a duration that is suitable to provide the desired effect. For example, contacting can be carried out once or multiple times, and in vivo administration can be carried out with a single sustained-release dosage formulation or with multiple (e.g., daily) doses.

The amount to be administered will, of course, vary depending upon the particular conditions and treatment regimen. The amount/dose required to obtain the desired effect may vary depending on the agent, formulation, cell type, culture conditions (for ex vivo embodiments), the duration for which treatment is desired, and, for in vivo embodiments, the individual to whom the agent is administered.

Effective amounts can be determined empirically by those of skill in the art. For example, this may involve assays in which varying amounts of the oligooxopiperazine of the invention are administered to cells in culture and the concentration effective for obtaining the desired result is calculated. Determination of effective amounts for in vivo administration may also involve in vitro assays in which varying doses of agent are administered to cells in culture and the concentration of agent effective for achieving the desired result is determined in order to calculate the concentration required in vivo. Effective amounts may also be based on in vivo animal studies.

The present invention may be further illustrated by reference to the following examples.

EXAMPLES

The following Examples are intended to illustrate, but by no means are intended to limit, the scope of the present invention as set forth in the appended claims.

Example 1

Synthesis of Oligooxopiperazines

The oligooxopiperazines were synthesized via solid phase synthesis as described in U.S. patent application Ser. No. 12/917,176 to Arora et al., which is hereby incorporated by reference in its entirety, as shown in Scheme 1 below.

Scheme 1

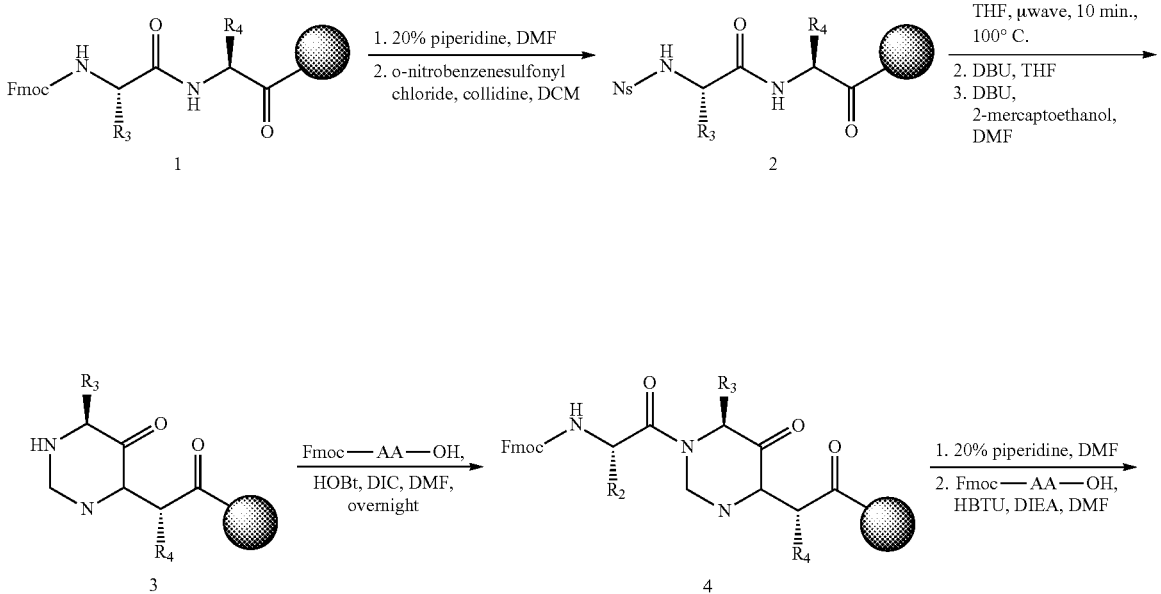

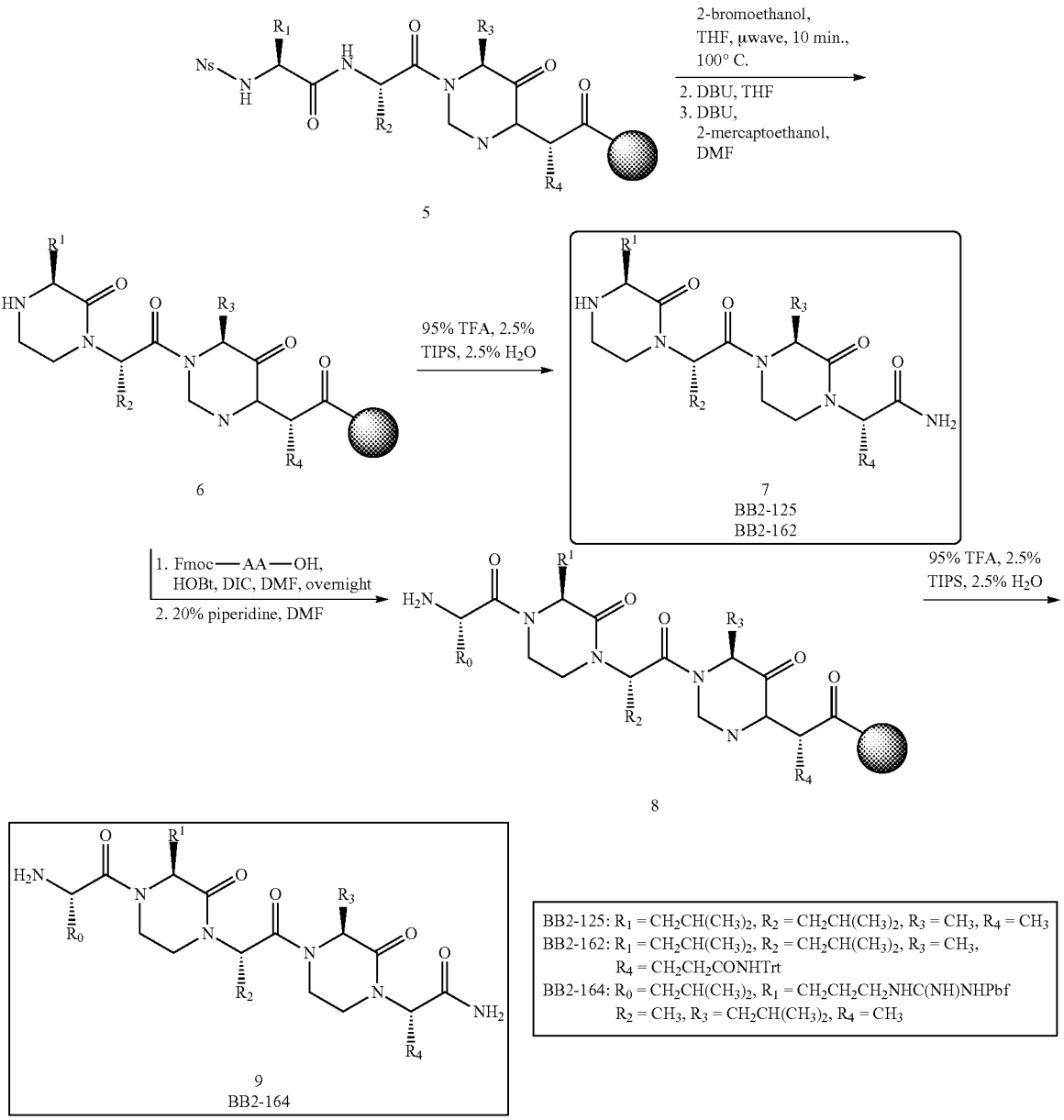

Dipeptide 1 was synthesized by standard Fmoc solid phase peptide synthesis on Knorr resin in a solid phase reaction vessel. The Fmoc group was removed by treatment with 20% piperidine in dimethylformamide (DMF) and the resin was washed sequentially with DMF, dichloromethane (DCM), methanol (MeOH), and diethyl ether and dried under vacuum. o-Nitrobenzenesulfonyl chloride (Ns-Cl, 10 eq) and collidine (10 eq) were dissolved in dry DCM and added to the reaction vessel. The mixture was shaken for 2 hours at 23° C. to obtain 2. The resin containing 2 was then washed sequentially with DMF, DCM, MeOH, and diethyl ether and dried for 12 hours under vacuum.

The resin containing 2 was transferred to a glass microwave tube (CEM). Triphenylphosphine (PPh$_3$, 5 eq) was added and the tube was flushed with nitrogen gas for 30 minutes. Tetrahydrofuran (THF), diisopropylazodicarboxylate (DIAD, 10 eq), and 2-bromoethanol (10 eq) were added and the reaction mixture was subjected to microwave irradiation (200 watts, 250 psi) for 10 minutes at 100° C. Resin was washed sequentially with THF, DMF, and DCM. Next, the resin was transferred to a solid phase vessel, treated with 1,8-diazabicyclo[5.4.0]undec-7-ene (DBU) in THF for 2 hours, then washed with THF, DMF, DCM, and diethyl ether and dried for 30 minutes followed by treatment with DBU and 2-mercaptoethanol in DMF for 2 hours. The resin, now containing 3, was washed with DMF, DCM, MeOH, and diethyl either and dried.

Figure 4:
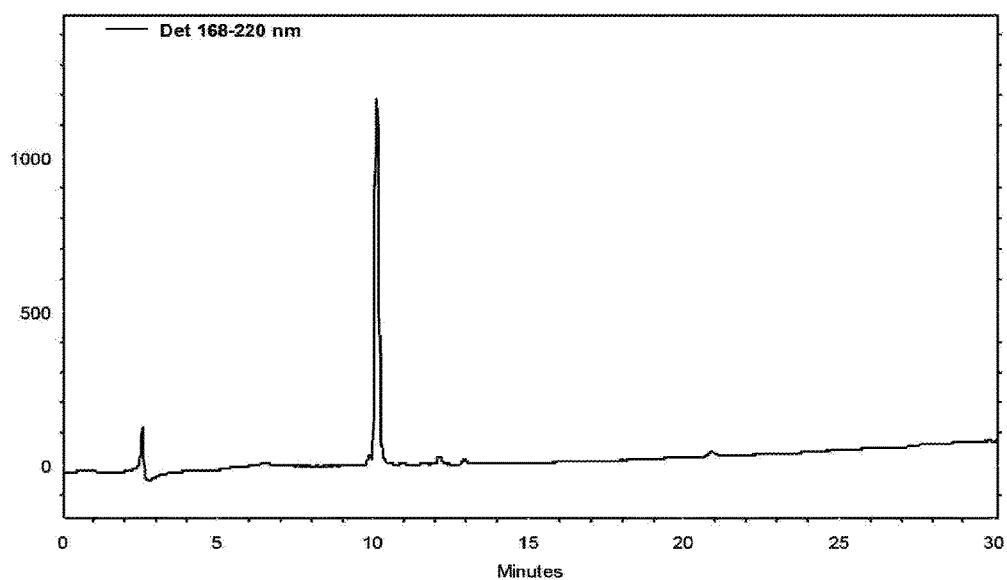
FIG. 4 is an analytical HPLC trace of BB2-125. Gradient: 5 to 95% acetonitrile/water in 30 minutes.
Figure 5:
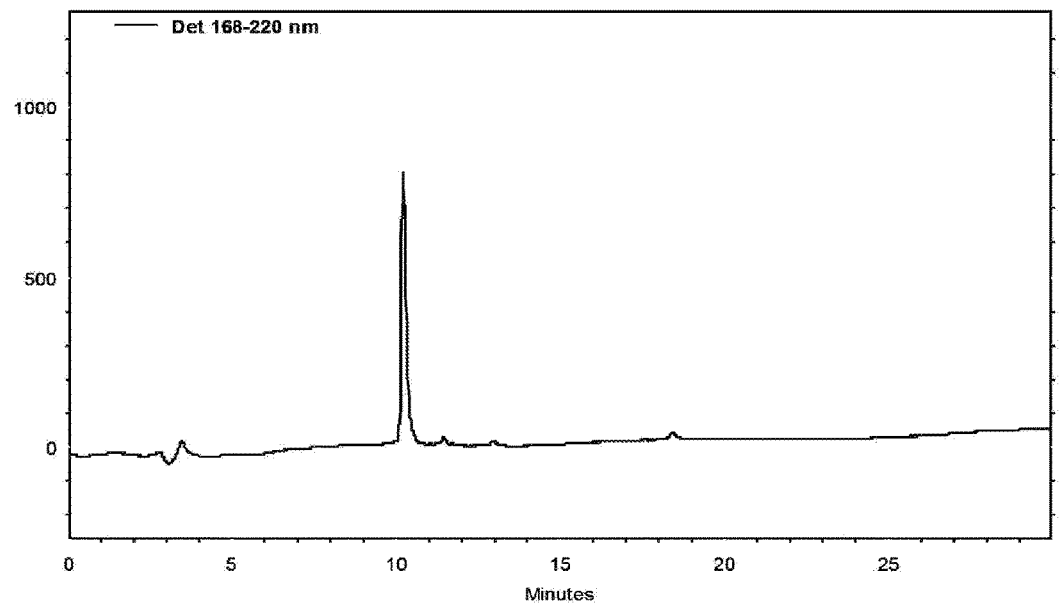
FIG. 5 is an analytical HPLC trace of BB2-162. Gradient: 5 to 95% acetonitrile/water in 30 minutes.
Figure 6:
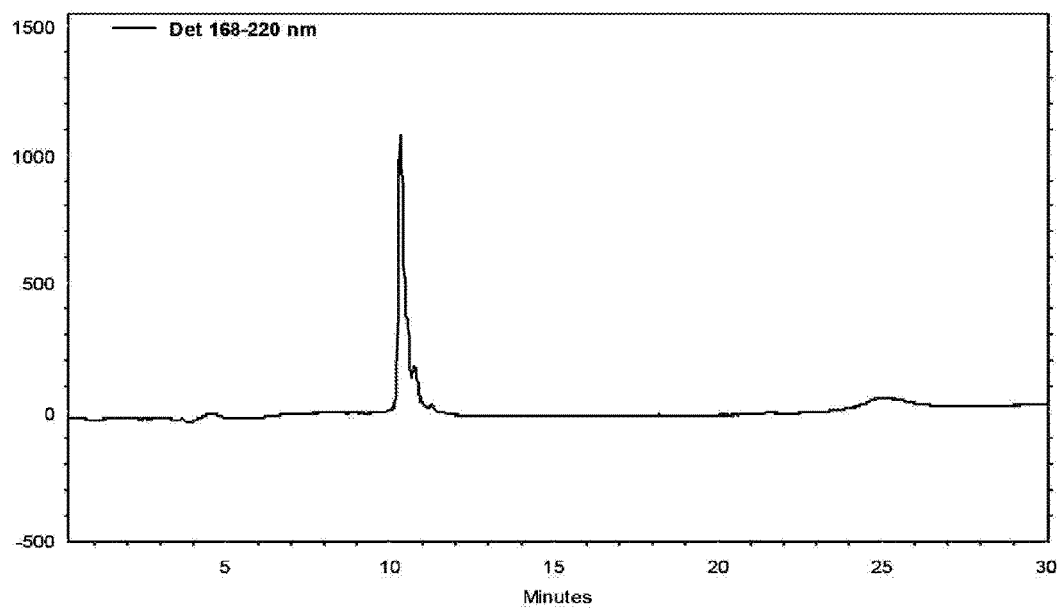
FIG. 6 is an analytical HPLC trace of BB2-164. Gradient: 5 to 95% acetonitrile/water in 30 minutes.

The desired pre-activated Fmoc-amino acid (Fmoc-AA-OH) was added to the resin containing 3 and the mixture was shaken at 23° C. for 12 hours. Nosyl protection and the ring formation steps were repeated to obtain oxopiperazine dimers BB2-125 and BB2-162 after cleavage from the resin with 95% trifluoroacetic acid (TFA), 2.5% water, and 2.5% triisopropylsilane (TIPS). For the formation of BB2-164, resin bound oxopiperazine dimer 6 was treated with a preactivated Fmoc-amino acid in DMF followed by cleavage from resin. Analytical HPLC traces for BB2-125, BB2-162, and BB2-164 are shown in FIG. 4, FIG. 5, and FIG. 6, respectively.

Example 2

MTT Cellular Viability

Human breast carcinoma (MCF7) or human lung carcinoma (A549) cells were seeded into 96-well plates (Greiner) at a density of 5,000-10,000 cells in 200 µL of the fresh media per well; MCF7 cells in RPMI media (Gibco) with 10% FBS (Irvine Scientific), A549 cells (ATCC) in F-12K media (ATCC) with 2% FBS (Irvine Scientific). The plates were then placed into the incubator (37° C., 5-10% $CO_2$) until the desired confluency (ca. 70%) was reached (ca. 24-72 hours). After that, the media in all the wells was replaced with a solution of BB2-125 or BB2-162 (150 µL for 48 hour study, 200 µL for 72 hour study, respectively) in the appropriate media. The plates were then maintained for 48 or 72 hours at 37° C., 5-10% $CO_2$, in the incubator. After 48 (or 72) hours of incubation with the compound, MTT (5 mg/ml in PBS, Sigma-Aldrich) was added into every well (10% v/v) and mixed carefully and thoroughly. The plates were further incubated for 3-4 hours at 37° C. and 5-10% $CO_2$, and then the media was removed carefully and completely. Resulting purple precipitate was dissolved in DMSO (200 µL/well) and the absorption of each well was measured at 562 nm using microplate reader (Synergy II, BioTek, Inc).

Example 3

Luciferase Transcription Assay

All the work was carried out in a biological hood with sterile supplies. MDA231-VEGF(HRE)-luc cells were seeded into 24-well plates (Greiner BioOne, 65,000 cells in 2 ml of G418 DMEM media (Gibco) with 10% FBS (Irvine Scientific) per well). The plates were placed into the incubator for 24 hours (37° C. and 5-10% $CO_2$). After that, the media in each well was replaced with a 10-µM or 20-µM solution of BB2-125, BB2-162, BB2-164, or a vehicle control (1 ml/well each) in the media (G418 DMEM, 10% FBS). The plates were incubated for 6 hours (37° C., 5-10% $CO_2$), then a solution of DFO (Sigma-Aldrich) in water (19.6 mg/ml, filtered through 0.2 micron Tuffryn filter (PALL), 10 µL per well) was added into the appropriate wells to induce hypoxia. The plates were incubated for 3 more hours (37° C., 5-10% $CO_2$), then the appropriate plate was placed into a plastic bag containing a damp paper towel and anaerobic pouch (BD GasPak EZ Pouch System) to induce hypoxia. The bag was then sealed (zip-lock) and placed into the incubator for 15 hours (37° C., 5-10% $CO_2$), for a total of 24 hours with the compound. 24 hours after dosing the cells with the compound, the media was removed from all the wells and the cells were washed with PBS buffer (once, 1 mL per well). Promega lysis buffer (Promega luciferase assay system E1500) was diluted (to 1×) and mixed with a protease inhibitor cocktail (Thermo Scientific, 100×), then added to the cells (150 µL/well). After 2 minutes the contents of every well was transferred into a separate cold Eppendorf tube, which was then kept on ice until the transfer was complete for the rest of the tubes. The tubes were centrifuged (2 min, 13,000 rpm, 4° C.). The supernatant from every tube was carefully transferred into three new ones (50 µL per tube). Samples were then stored at −70° C. One aliquot of every sample was taken out of the freezer and thawed. The aliquot (20 µL) was mixed with the luciferase assay reagent (100 µL, Promega luciferase assay system E1500) and the reading was taken immediately with a luminometer (Turner TD-20E). Concentration of the protein in every aliquot was determined with the BCA assay (BCA assay kit, Thermo Scientific) using a plate reader (Synergy II, BioTek, Inc). Each luminometer reading was normalized by the total protein concentration of the sample.

Example 4 mRNA Transcription Assay

The ability of the oligooxopiperazines to alter transcriptional activity was also evaluated using an mRNA isolation experiment (Qiagen RNeasy Mini kit). MCF7 and A549 cells were seeded into 6-well plates (Greiner BioOne; MCF7 cells: 300,000 cells/well in RPMI media (Gibco) with 10% FBS (Irvine Scientific); A549 cells (ATCC): 200,000 cells/well in F-12K media (ATCC) with 2% FBS (Irvine Scientific)). The plates were then placed into an incubator for 24 hours (37° C., 5-10% $CO_2$).

At 70-80% confluency (after 24-48 hours) the media was replaced with a solution of chetomin (~100 nM), BB2-125 (5 or 10 µM), BB2-162 (5 or 10 µM) BB2-164 (20 µM), or a vehicle control in the corresponding media (MCF7 cells: RPMI media with 10% FBS, A549 cells: F-12K media with 0.2% FBS). The plates were incubated for 6 hours (37° C., 5-10% $CO_2$), then a solution of DFO (Sigma-Aldrich) in water (19.6 mg/ml, filtered through 0.2 µm Tuffryn filter (PALL), 10 µL per well) was added into the appropriate wells to induce hypoxia. The plates were incubated for 3 more hours (37° C., 5-10% $CO_2$), then the appropriate plate was placed into a plastic bag containing a damp paper towel and an anaerobic pouch (BD GasPak EZ Pouch System) to induce hypoxia. The bag was then sealed (zip-lock) and placed into an incubator for 15 hours (37° C., 5-10% $CO_2$), for a total of 24 hours with the compound.

24 hours after dosing the cells with the compound, the media was removed from all the wells and the cells were washed with PBS buffer (twice, 1 ml per well). RLT buffer with 1% v/v of β-mercaptoethanol (350 µl/well) was added to the wells in order to lyse the cells. The cellular residues were carefully scraped off with a pipette tip and the lysate was then transferred from every well into a separate 1.5 ml collection tube (Ambion). The wells were washed with ethanol solution (70% in water, 400 µL/well), one well at a time, and then the washings were transferred into the respective collection tube and the contents of the tube were mixed well by pipetting up and down until a homogenous solution with low viscosity was observed. The lysate was then transferred from the collection tubes into the RNeasy spin columns, placed into the 2 ml collection tube. The columns were centrifuged (15 sec, 13000 rpm, rt) and the flow through was discarded. RW1 buffer (700 µL) was added to each RNeasy column and the columns were centrifuged (15 sec, 13000 rpm, rt), the flow through was discarded. RPE buffer (20% solution in absolute ethanol, 500 µL) was added to each RNeasy column and the columns were centrifuged (15 sec, 13000 rpm, rt), the flow through was discarded, and another washing with PRE buffer was carried out. RNeasy columns were placed into new 2 ml collection tubes and centrifuged (1 min, 13000 rpm, rt). The flow through and the collection tubes were discarded. RNeasy columns were placed into new 1.5 ml collection tubes and mRNA was eluted with RNase free water (50 µl/sample), added directly into the center of each column, followed by centrifugation (2 min, 13000 rpm, rt). The RNA was stabilized with RNAsin (Promega, 0.5 µL/sample).

To remove the residual genomic DNA, Turbo DNase buffer (10×, 5 µL) and Turbo DNase (1 µL) were added to each sample. Samples were incubated at 37° C. for 30 minutes. DNA inactivation reagent was resuspended by vortexing and added (5 µL) to each sample. Samples were incubated at room temperature for 5 minutes, then centrifuged (2 min, 13000 rpm, rt). The supernatant (solution of mRNA) was transferred into new collection tubes (Ambion). The mRNA samples were diluted 20 or 40 times (depending on the expected concentration range) and the mRNA concentration was determined by the UV-spectroscopy (absorption at 260 nm).

To prepare cDNA (Superscript III Reverse Transcriptase protocol, Invitrogen), mRNA (11 µL) was mixed with Oligo $(dT)_{18}$ (1 µL), Random Primers (1 µL), and dNTP mix (1 µL). The mixture was heated at 65° C. for 5 minutes and then held at 4° C. for at least 1 minute (PxE-0.2 Thermal Cycler), then the tubes were centrifuged for 15 seconds at 13,000 rpm. The First strand buffer (5×, 4 µL), DTT (0.1 M, 1 µL) and Superscript III RT (1 µL) were mixed into each sample, then the samples were incubated at 25° C. for 5 minutes, then at 50° C. for 60 minutes, and finally at 70° C. for 15 minutes to inactivate the reaction. Samples of the cDNA were stored at −80° C. in the freezer.

Example 5

Western Blotting

A549 cells were seeded into 6-well plates (200,000/well). The cells reached ca. 70-80% confluency after 42-44 hours. The medium in all wells was then replaced with fresh medium containing DMSO (0.1% v/v) and the appropriate concentration of the oligooxopiperazines. Every well in one plate was treated in the same way. Following 6 hours of incubation at 37° C. (5% $CO_2$), hypoxia was induced by placing appropriate plates into the BD GasPak Anaerobic EZ Pouch. The cells were then returned into the incubator for an additional 18 or 42 hours.

After the incubation was over, all plates were placed on ice. The cells were then washed with ice-cold PBS (1 ml/well, twice) and then lysed with Promega luciferase assay lysis buffer (diluted with water to 1× concentration and supplemented with ThermoScientific Halt Protease Inhibitor cocktail) at ambient temperature: 300 µl of lysis buffer were used to harvest and merge the cell lysate from all the wells in one plate into one pre-chilled 1.5 ml PP tube. The tubes with the lysate were centrifuged for 10 minutes. The supernatant in each tube was carefully collected, aliquoted into two 0.5 ml PP tubes, and frozen at −80° C.

Protein concentration in each sample was determined by the BCA assay, then the samples were mixed with 4× Laemmli loading buffer. Polyacrylamide gel (12%) was cast and 30 µg of total protein of each sample was loaded into the gel. SDS-PAGE was performed (10 minutes at 120 V, then ca. 1 hour at 140 V). After that, the proteins from each gel were transferred onto the PVDF membrane. Wet transfer was conducted in the Towbin buffer (192 mM glycine, 25 mM tris, 20% MeOH v/v) for 1.5-2 hours, in the ice bath and the assembly was placed into the fridge at 4° C.

After the transfer, the membrane was washed with TBST buffer for 10 minutes, then blocked with milk (5% w/v in TBST buffer, rocking, ambient temperature, 1 hour). The membrane was then rinsed with TBST buffer and then immediately incubated with primary antibody (1% milk in TBST, 4° C., gentle rocking, overnight). The next day, the membrane was washed with TBST buffer (3 times, 5 minutes each) and then incubated with appropriate secondary antibody (1% milk in TBST, gentle rocking, ambient temperature, 1 hour) and after that washed again with TBST buffer (3×, 10 minutes each). The membrane was treated with ECL solution for 3 minutes (Ambion) and then the X-ray film was exposed to the membrane. The results were quantified with ImageJ software (Primary antibodies: anti-HIF-1α BD Biosciences, mouse, 610959, lot #23681, 1:750; anti-c-Met (D1C2) XP, Cell Signaling, rabbit, #8198P, lot #1, 1:2000; anti-β-actin, Cell Signaling, rabbit, 4967S, lot 6, 1:2000. Secondary antibodies: goat anti-mouse HRP-labeled Santa Cruz, IgG-HRP, sc-2005, lot #E0112, 1:2000; bovine anti-rabbit HRP-labeled Santa Cruz, IgG-HRP, sc-2379, lot #A1612).

Figure 20:
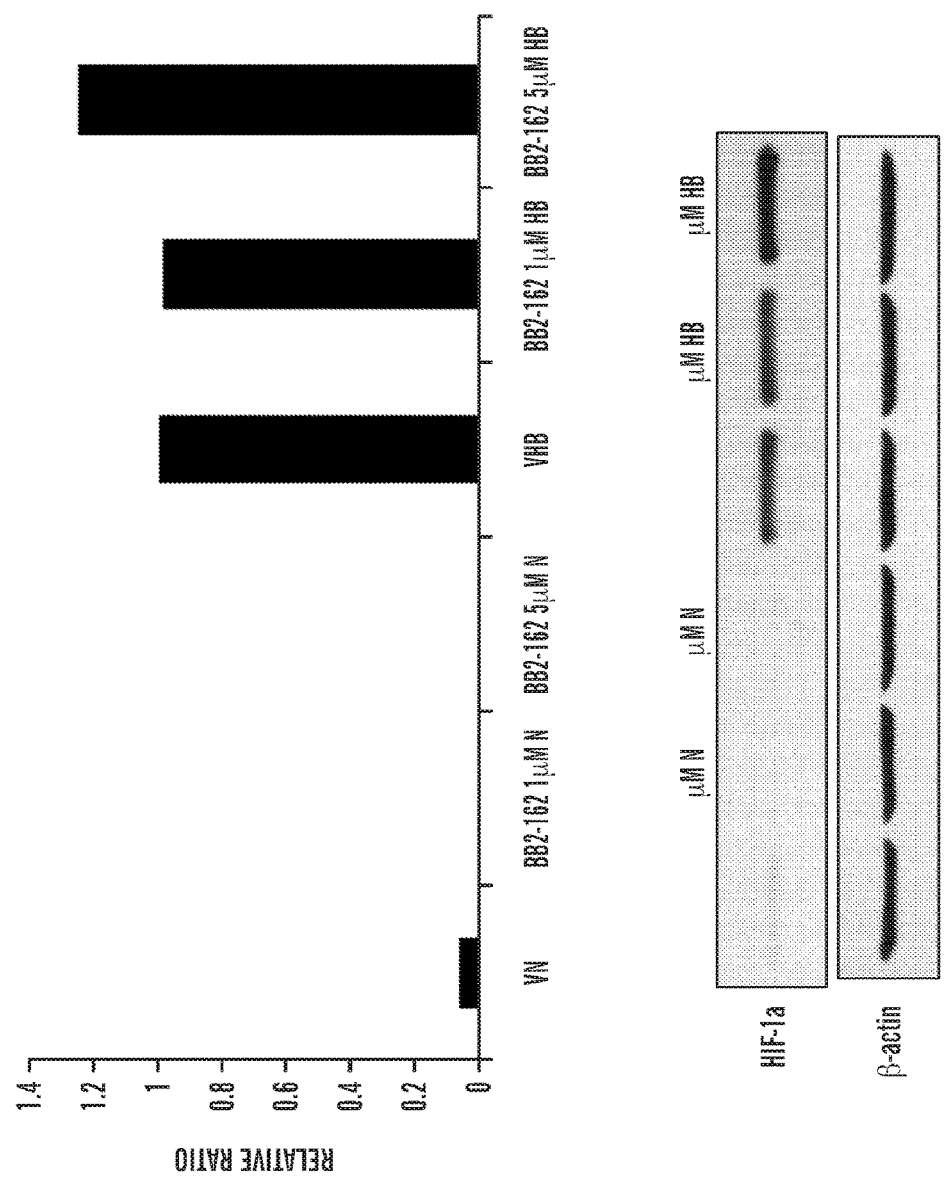
FIG. 20 is a graph (upper panel) and western blots (lower panels) showing the ratio of the relative levels of HIF-1α to the relative levels of β-actin in A549 cells after 48 hours of treatment with BB2-162 in normoxia and hypoxia (42 hours), 0.2% FBS in media. V N: cells treated with vehicle control under normoxic conditions; BB2-162 1 μM N: cells treated with 1 μM BB2-162 under normoxic conditions; BB2-162 5 μM N: cells treated with 5 μM BB2-162 under normoxic conditions; V HB: cells treated with vehicle control under hypoxic conditions; BB2-162 1 μM HB: cells treated with 1 BB2-162 under hypoxic conditions; BB2-162 5 μM HB: cells treated with 5 BB2-162 under hypoxic conditions.
Figure 21:
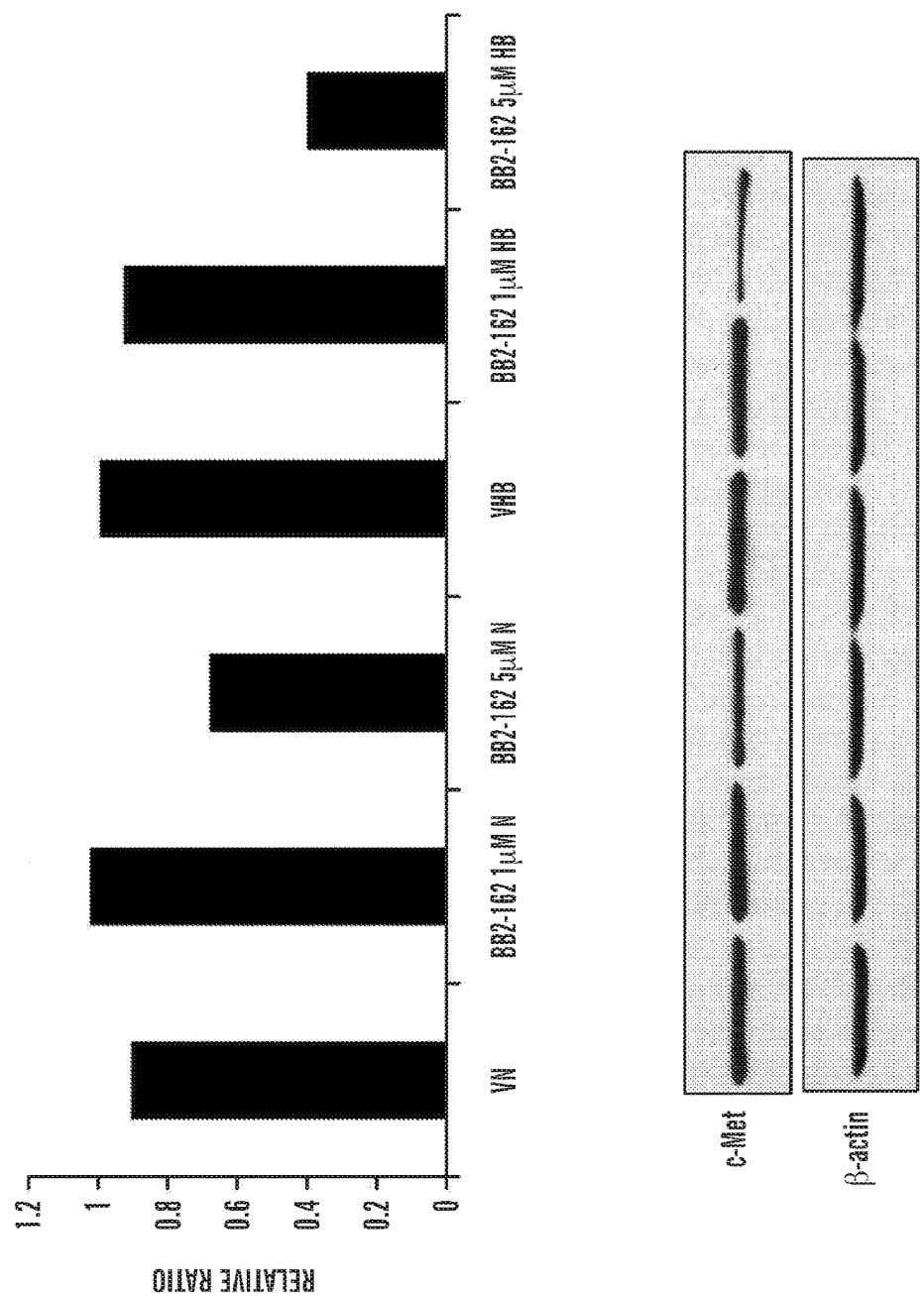
FIG. 21 is a graph (upper panel) and western blots (lower panels) showing the ratio of the relative levels of c-Met to the relative levels of β-actin in A549 cells after 48 hours of treatment with BB2-162 in normoxia and hypoxia (42 hours), 0.2% FBS in media. V N: cells treated with vehicle control under normoxic conditions; BB2-162 1 μM: cells treated with 1 μM BB2-162 under normoxic conditions; BB2-162 5 μM N: cells treated with 5 μM BB2-162 under normoxic conditions; V HB: cells treated with vehicle control under hypoxic conditions; BB2-162 1 μM HB: cells treated with 1 μM BB2-162 under hypoxic conditions; BB2-162 5 μM HB: cells treated with 5 μM BB2-162 under hypoxic conditions.

A549 cells were treated with BB2-162 under normoxic and hypoxic conditions as described above and examined for levels of HIF and cMet. As shown in FIGS. 20-21, as expected, the HIF protein levels were unaffected by BB2-162, but cMet levels were decreased in the cells treated with BB2-162. This confirms that the compound targets HIF-mediated transcription but not levels of HIF itself.

Discussion of Examples 1-5

Figure 7:
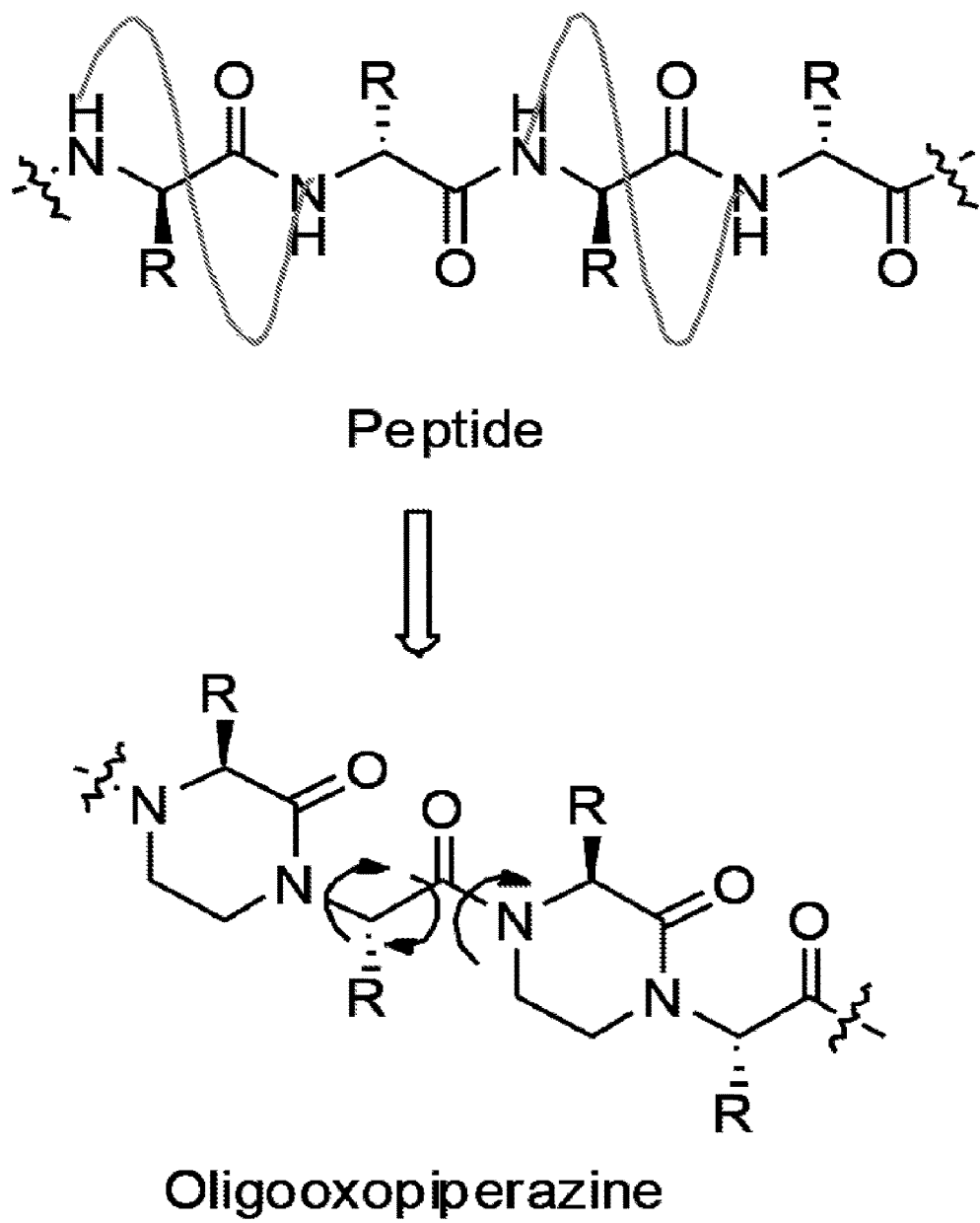
FIG. 7 illustrates the design of amino acid-derived oligooxopiperazines (Tosovska & Arora, *Org. Lett.* 12:1588 (2010)). The oligooxopiperazines are obtained by linking neighboring amide nitrogen atoms in peptides with ethylene bridges, as depicted.

Oligooxopiperazines are non-peptidic helix mimetics that feature a chiral backbone (see FIG. 7). These compounds are easily synthesized from α-amino acids allowing rapid diversification of the scaffold. Conformational analysis of oxopiperazine dimers and trimers composed of α-amino acids suggests that these compounds span the length of 7-10mer α-helices. Crystal structures of related compounds, quantum mechanical calculations, and molecular mechanics simulations have been used to better understand the conformation of the oxopiperazine scaffold. Results support the hypothesis that oligooxopiperazines provide a stable and geometrically appropriate helix mimetic.

Figure 8:
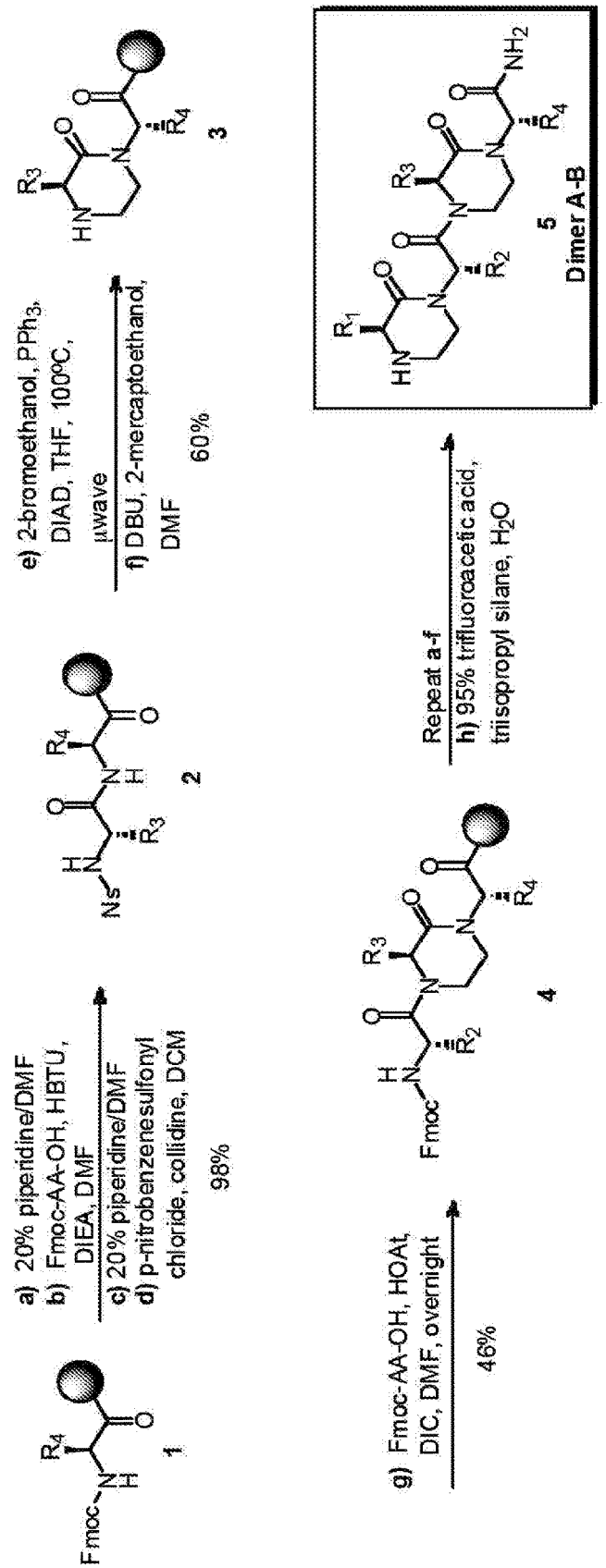
FIG. 8 is a general synthesis scheme for making oligooxopiperazines using microwave-assisted solid phase synthesis.

As shown in FIG. 8, an efficient microwave-assisted solid phase synthesis of oxopiperazine oligomers has been developed (U.S. patent application Ser. No. 12/917,176 to Arora et al., which is hereby incorporated by reference in its entirety). The key step in the synthesis involves ring closure, and Mitsunobu conditions with nosyl-protected amino acid residues was found to offer the highest yields.

Figure 9:
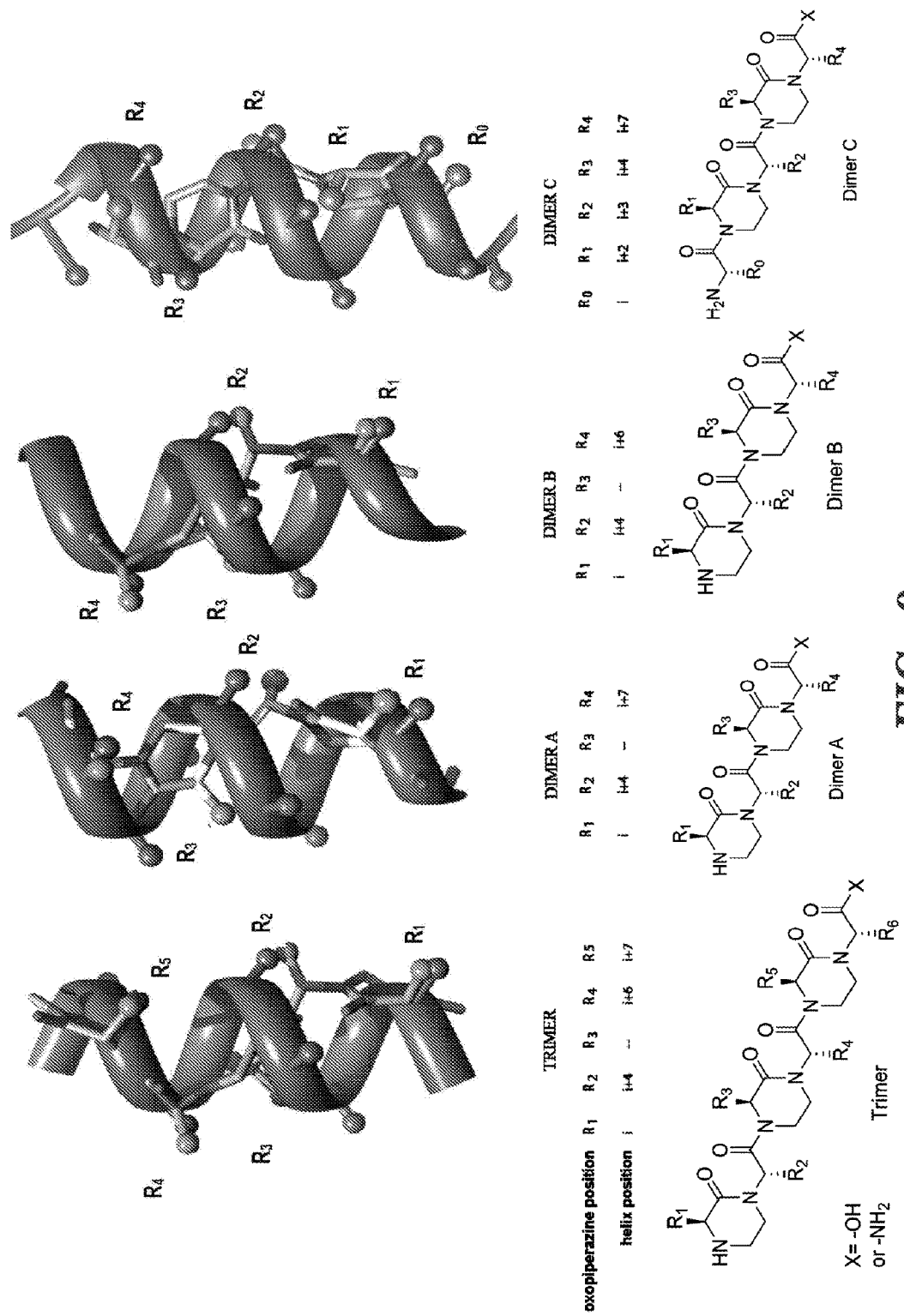
FIG. 9 shows the design and structure of model oligooxopiperazine dimers A-C and a model oligooxopiperazine trimer. An overlay of the predicted structure of each model oligooxopiperazine and its target α-helix is also shown.

As shown in FIG. 9, four potential options—based on the predicted lowest energy conformation—for the design of oligooxopiperazines to mimic functionality on one face of a two-turn helix were contemplated. These configurations are termed "Dimers A-C" and "Trimer" in FIG. 9. The Dimer configurations differ from each other in the overlay of oxopiperazine residues on to the canonical helix; Dimer C contains an extra N-terminal residue. In Dimer A and B, oxopiperazine positions $R_1$ and $R_2$ overlay onto the i and i+4 residues whereas in Dimer C positions $R_1$ and $R_3$ overlay with these positions. Dimers A and B differ in the relative positioning of the axis of the oxopiperazine scaffold; their overlays suggest that $R_4$ may align with the i+6 or the i+7 residues. Dimer C design uses a different alignment, with an N-terminal amino acid residue providing the first contact.

Figure 10:
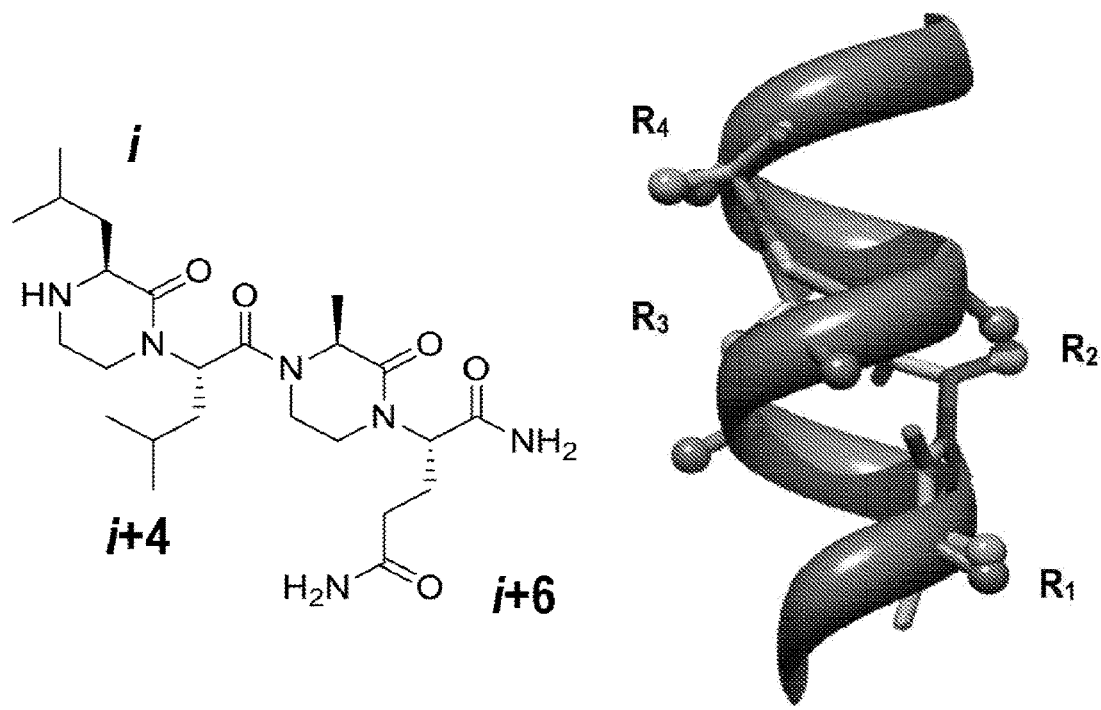
FIG. 10 shows the design and structure of a model oligooxopiperazine dimer B that mimics the αB helix of HIF-1α.
Figure 11:
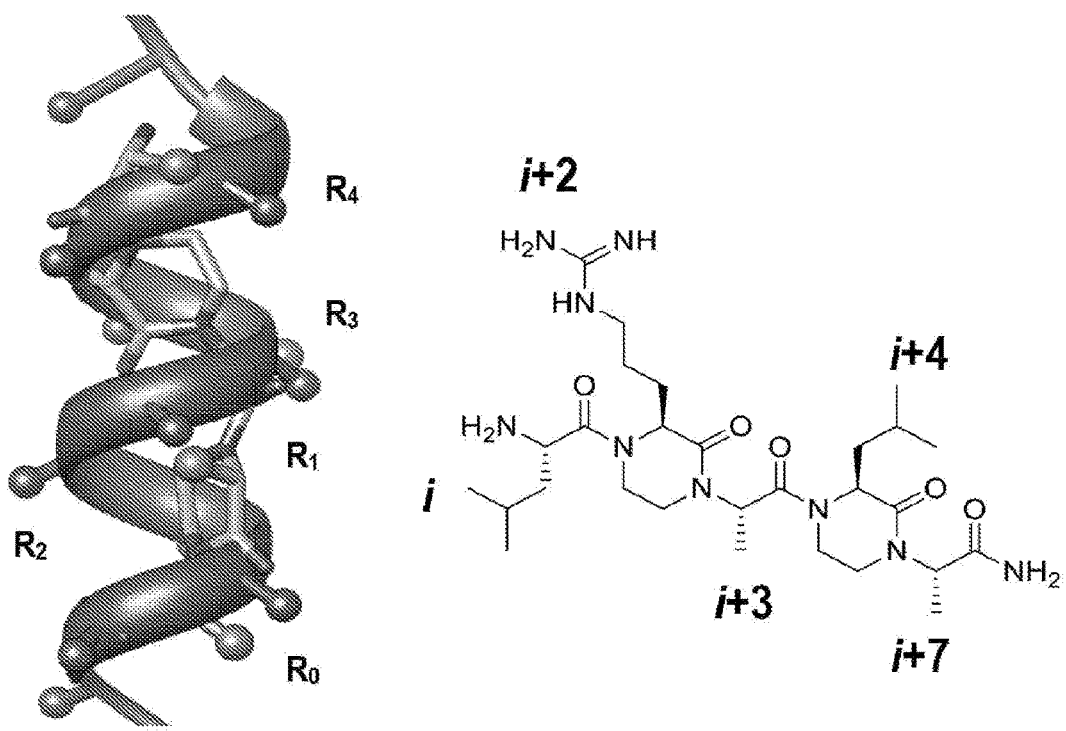
FIG. 11 shows the design and structure of a model oligooxopiperazine dimer C that mimics the αB helix of HIF-1α.
Figure 12:
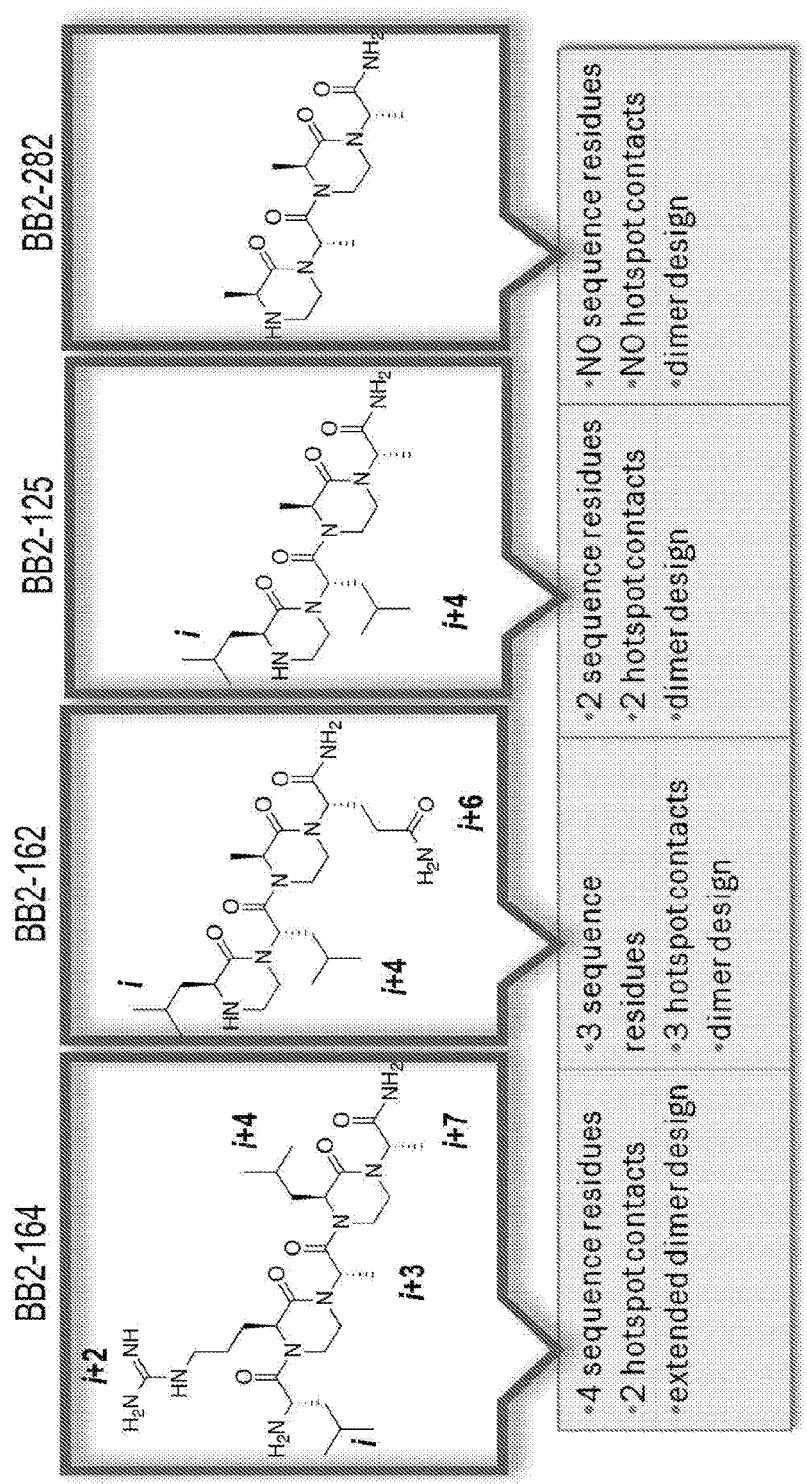
FIG. 12 shows oligooxopiperazines BB2-164, BB2-162, BB2-125, and BB2-282.
Figure 13:
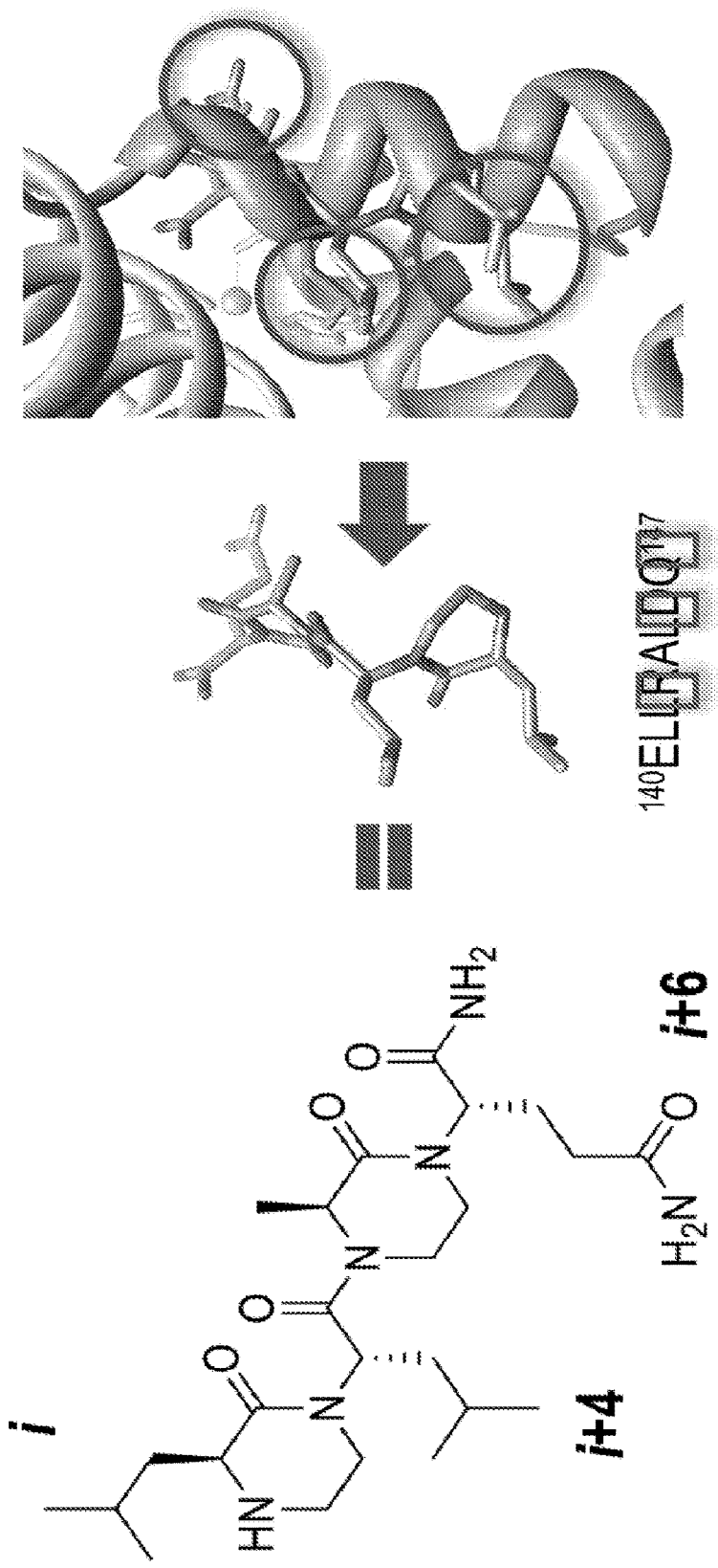
FIG. 13 illustrates the design of oligooxopiperazine BB2-162. The sequence of helix αB (SEQ ID NO: 2) is also shown with a box around each hotspot residue.

As described herein and illustrated in FIG. 10 and FIG. 11, HIF-1α mimetics for dimer B (FIG. 10) and dimer C (FIG. 11) helical overlays have been designed. As shown in FIG. 12, four analogs were designed based on computational analysis. BB2-164 oligooxopiperazine is based on the dimer C design. BB2-162 is based on the dimer B design. BB2-125 is a negative control of BB2-162, where the glutamine residue is replaced with an alanine group. BB2-282 is also a negative control and displays no critical residues. In designing mimetics, the natural amino acid sequence of helix αB (PDB code IL8C, residues 139-147) HIF-1α was utilized, as illustrated in FIG. 13. FIG. 13 shows an overlay of oligooxopiperazine BB2-162 and helix αB.

Figure 14:
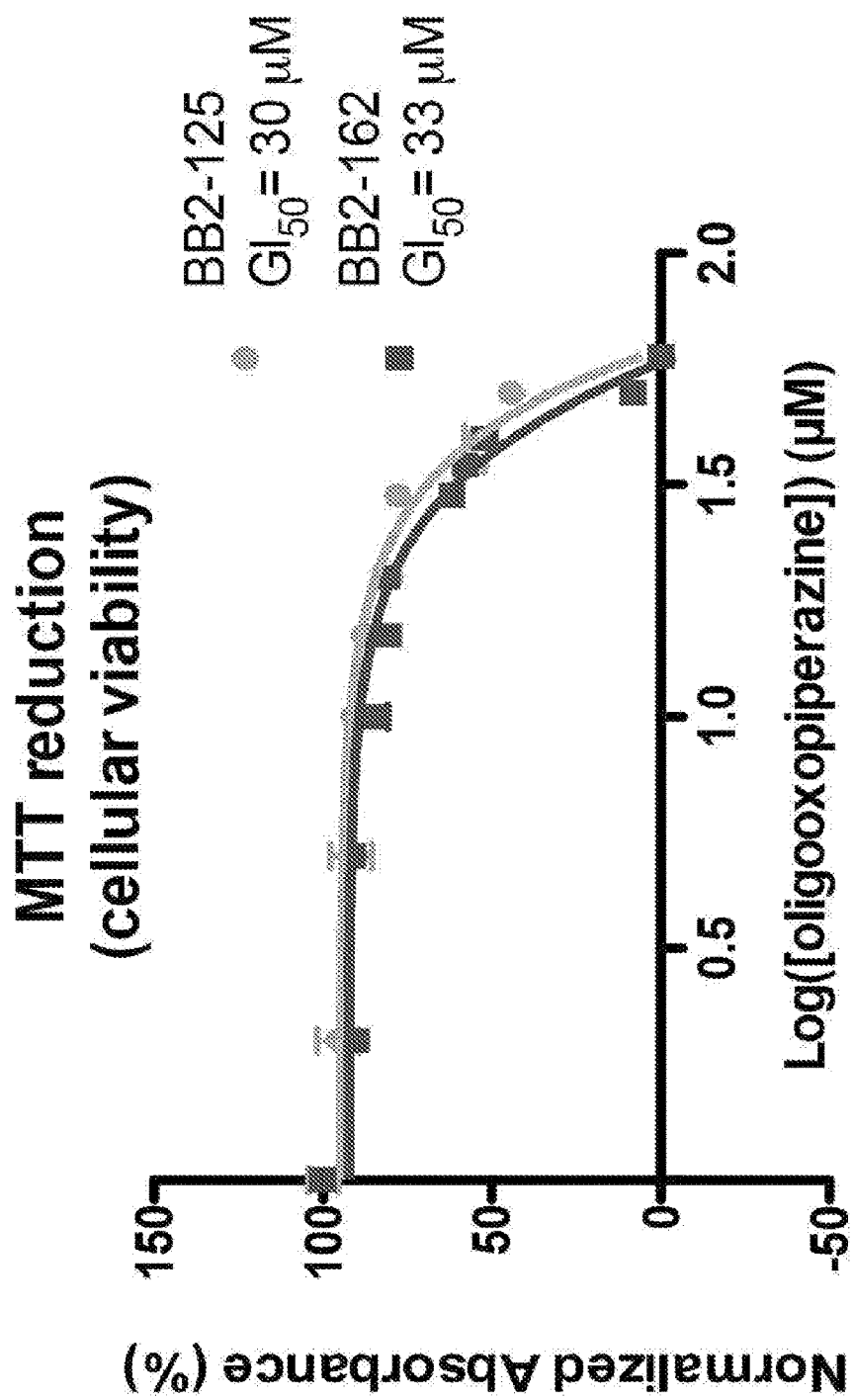
FIG. 14 is a graph of cellular viability upon exposure to varying concentrations of oligooxopiperazines BB2-125 or BB2-162.

Cellular viability MTT assays were performed to evaluate the toxicity of the oligooxopiperazines. As shown in FIG. 14, oligooxopiperazines exert no toxic effect on HeLa cells up to concentrations of 20 μM, with $GI_{50}$ values of 30 μM.

Figure 15:
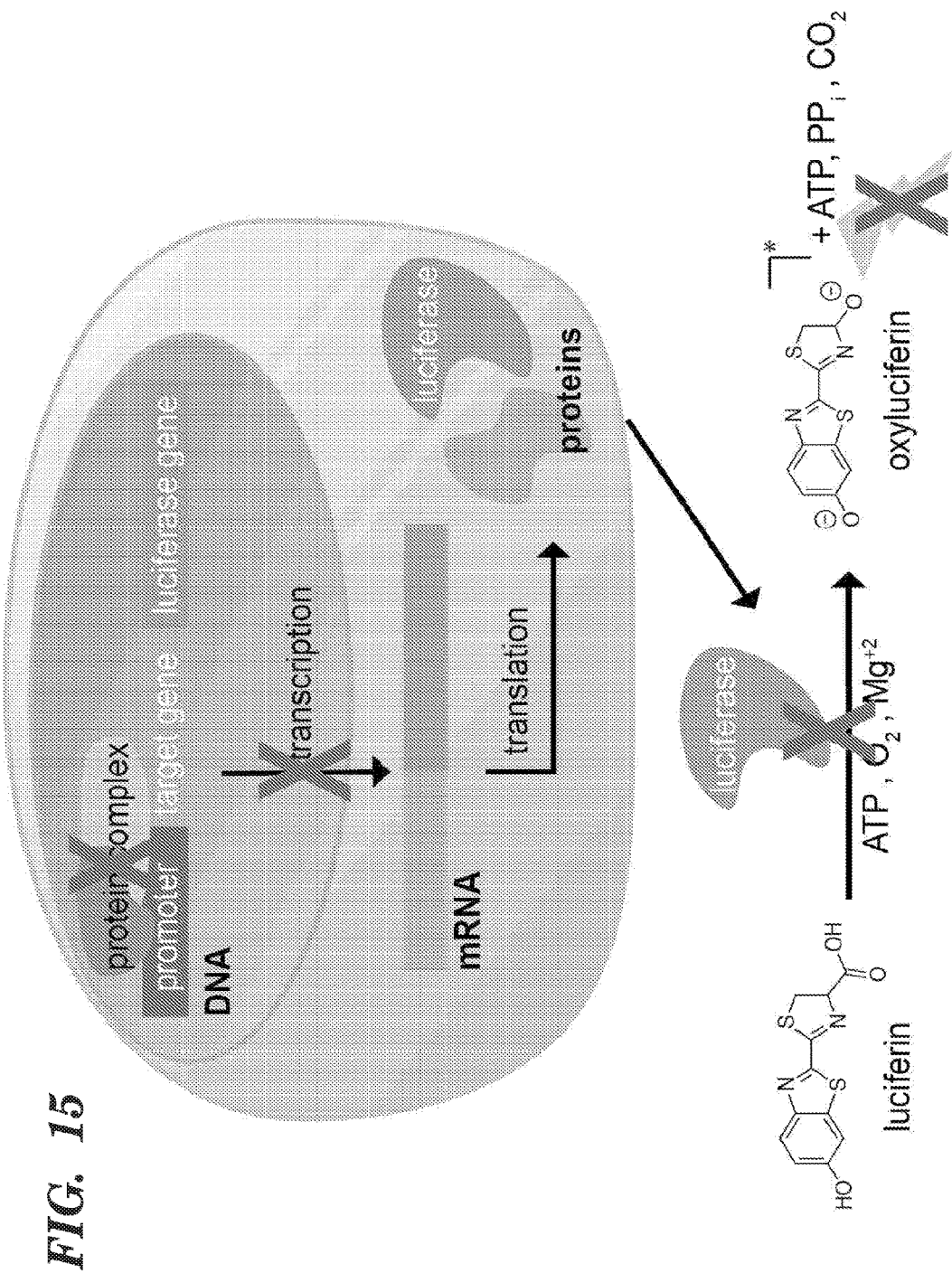
FIG. 15 is a schematic illustration (adapted from www-.berthold.com) of how the luciferase reporter assay is used to quantify the ability of an agent to downregulate transcription of a target gene.
Figure 16:
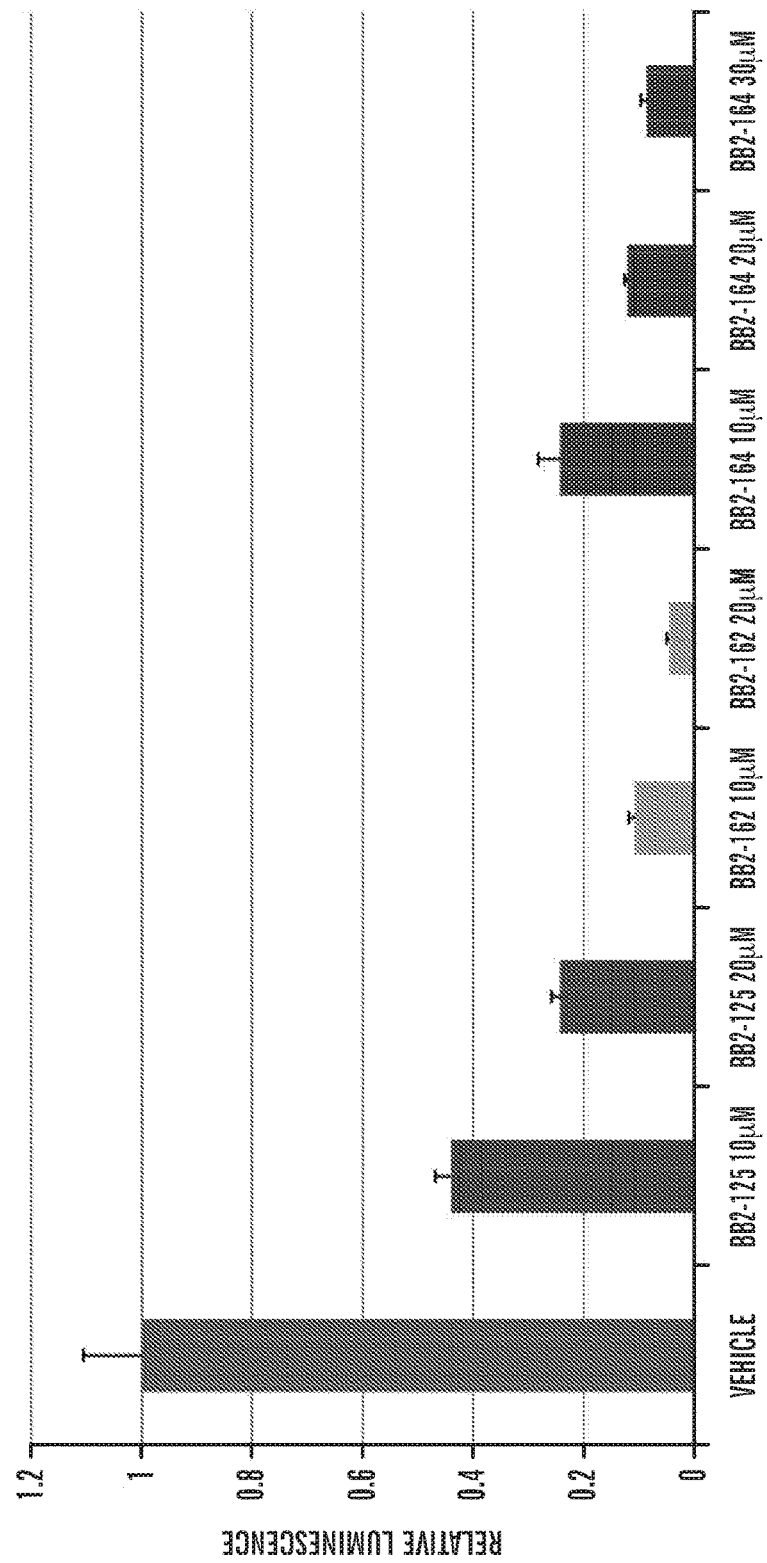
FIG. 16 is a graph of relative luminescence, corresponding to the level of transcription of VEGF in MDA231-VEGF-luc cells upon exposure to a vehicle control or varying concentrations of BB2-125, BB2-162, BB2-164.

A luciferase reporter assay, where the VEGF gene product is fused with luciferase (MDA231-VEGF-luc), was used to quantify the ability of oligooxopiperazines to enter cells and downregulate transcription of VEGF mediated by HIF-1α, as illustrated in FIG. 15. As shown in FIG. 16, concentration-dependent reduction in the levels of VEGF-luciferase product was observed with BB2-125, BB2-162, and BB2-164. At 20 μM concentrations, BB2-125 blocks luciferase transcription by roughly 75%. In comparison, BB2-164 blocks transcription by 88% and BB2-162 by 95%. Thus, BB2-162 and BB2-164 are potent inhibitors of HIF-1α transcription. The negative control is less active, as designed, but each of the tested oligooxopiperazines reduced transcription by at least 50%. Notably, this reduction was achieved using only 10 or 20 μM concentrations. This is the first known demonstration of a HIF-1α target achieving significant transcription reduction at non-toxic levels.

Figure 17:
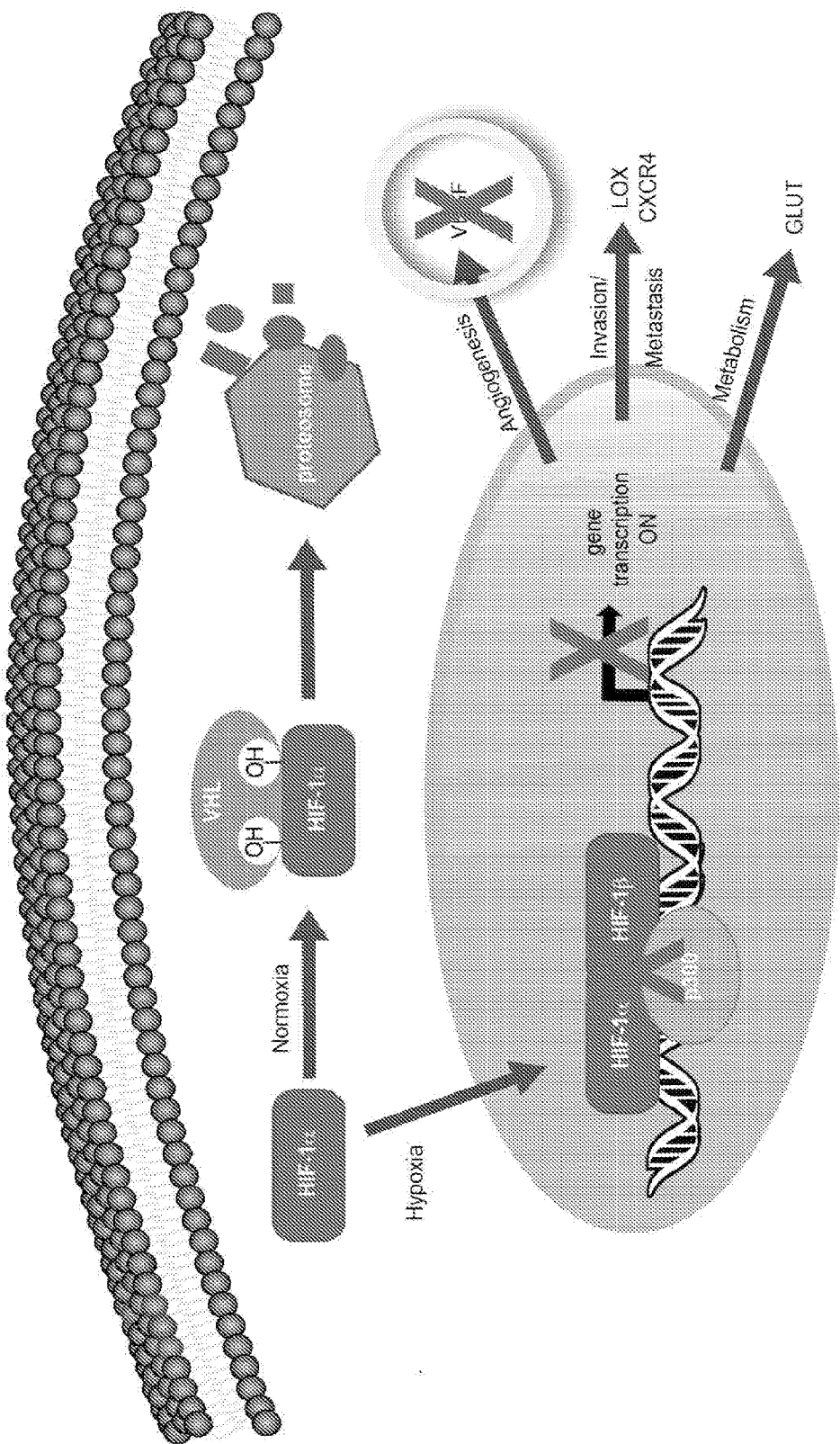
FIG. 17 is a schematic illustration of HIF-1α-mediated regulation of oxygen-dependent transcription, showing the reduction of VEGF production by disruption of the HIF-1α-p300 interaction (Rankin & Giaccia, *Cell Death Different.* 15:678 (2008)).
Figure 18:
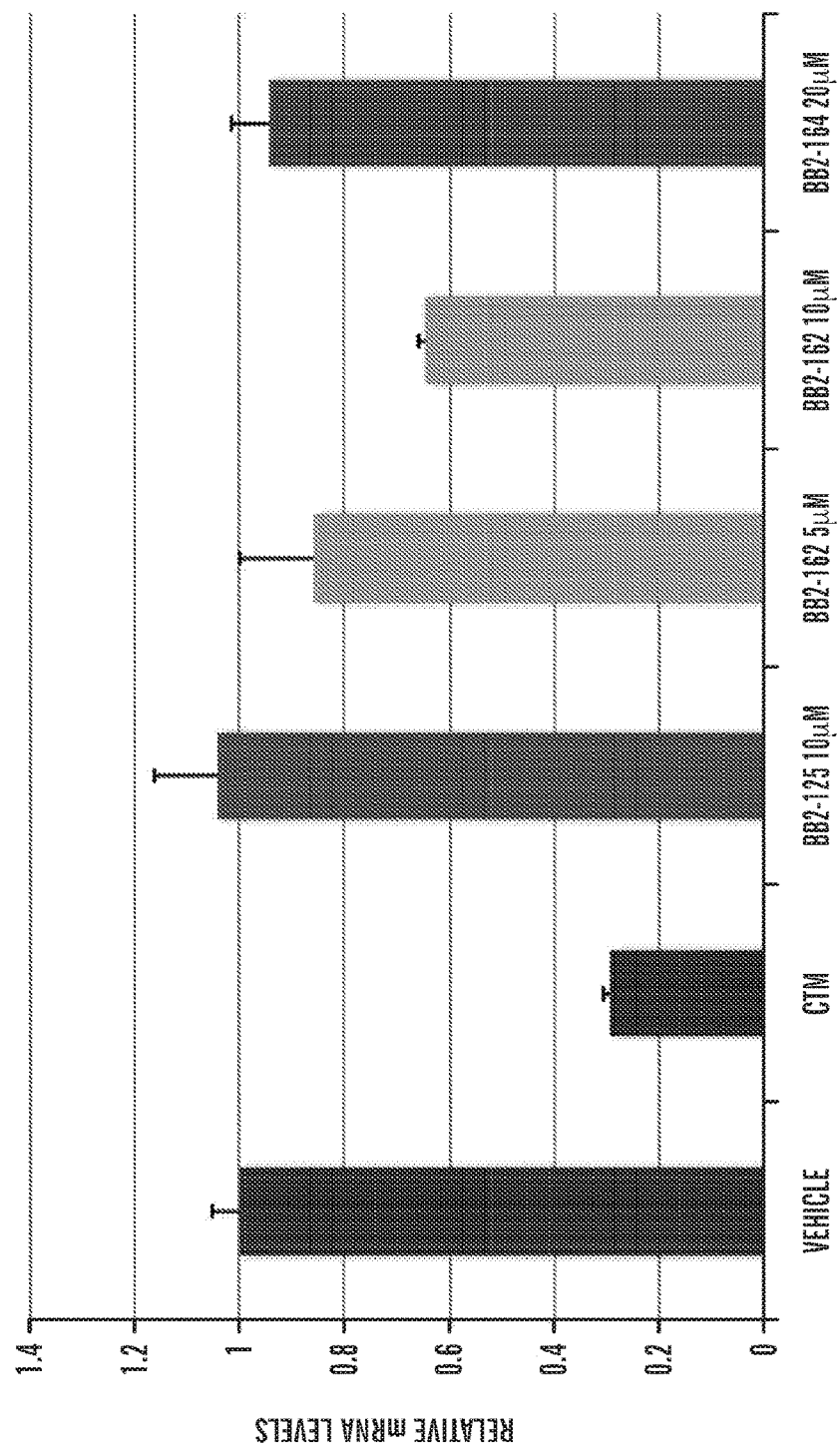
FIG. 18 is a graph of the relative mRNA levels of VEGF in cells treated with a vehicle control, chetomin ("CTM"), BB2-125, BB2-162, or BB2-164.
Figure 19:
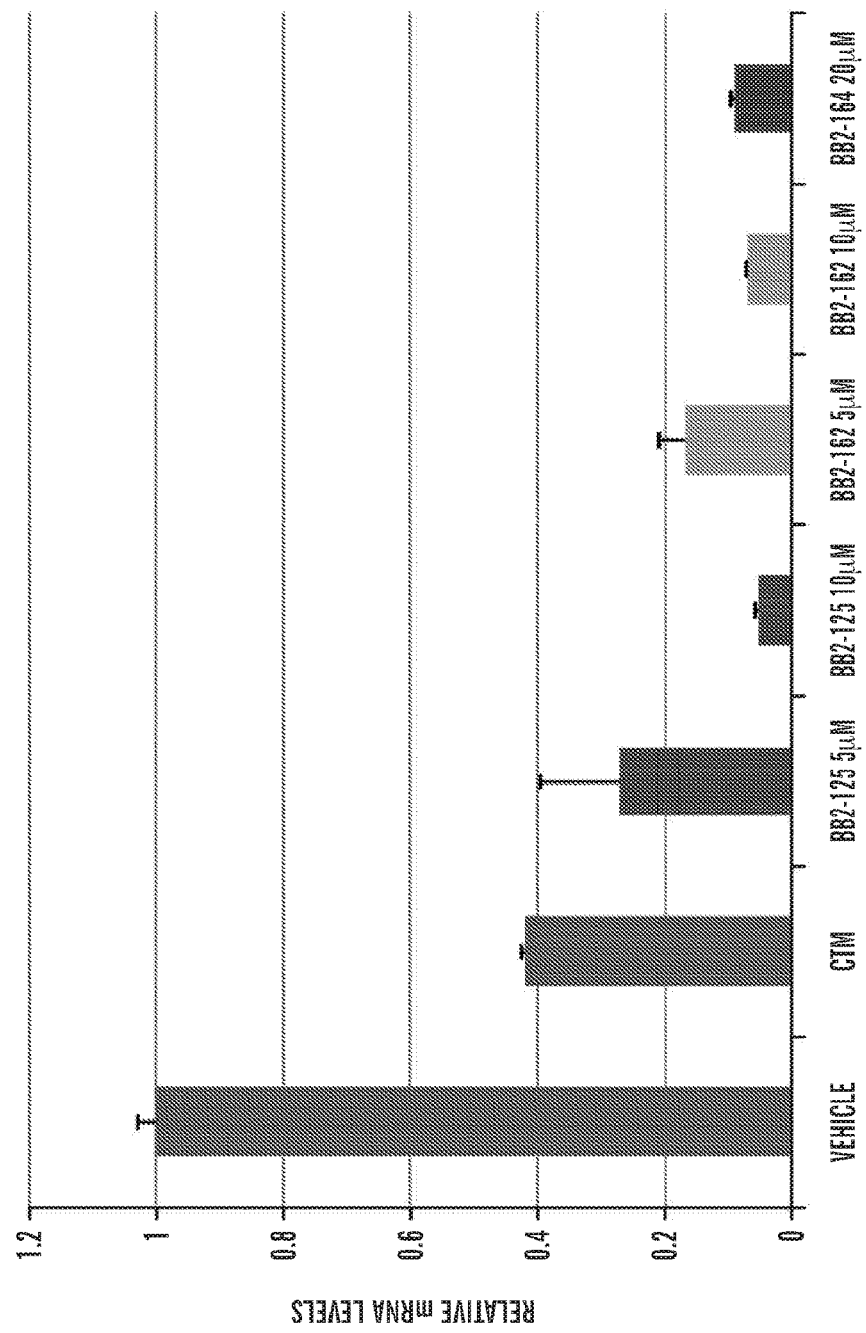
FIG. 19 is a graph of the relative mRNA levels of LOX in cells treated with a vehicle control, chetomin ("CTM"), BB2-125, BB2-162, or BB2-164.

A quantitative RT-PCR assay was used to establish the effect of the designed compounds on cellular levels of VEGF in response to inhibition of the transcription factor/coactivator complex formation (see FIG. 17). As shown in FIG. 18, BB2-162 lowers the levels of VEGF by 20% and 40% at 5 and 10 μM concentrations, respectively. BB2-164 and BB2-125 have smaller effects on VEGF mRNA levels. Chetomin (CTM) was used as a positive control. Chetomin is known to inhibit HIF-1α transcription but does so by non-specifically denaturing Zn-containing proteins (including p300/CBP) (Cook et al., "Epidithiodiketopiperazines Block the Interaction Between Hypoxia Inducible Factor-1α (HIF-1α) and p300 by a Zinc Ejection Mechanism," *J. Biol. Chem.* 284:M109.009498 (2009); Kung et al., "Small Molecule Blockade of Transcriptional Coactivation of the Hypoxia-Inducible Factor Pathway," *Cancer Cell* 6:33-43 (2004), each of which is hereby incorporated by reference in its entirety), and is toxic at effective concentrations. Interaction of HIF-1α with p300/CBP controls transcription of several genes. For example, as shown in FIG. 19, levels of LOX were also found to be downregulated by all three compounds.

These experiments demonstrate that oligooxopiperazine mimics of helix αB of HIF-1α can effectively inhibit transcription of hypoxia-inducible genes, and these effects can be achieved at non-toxic concentrations.

What is claimed is:

1. An oligooxopiperazine of Formula I:

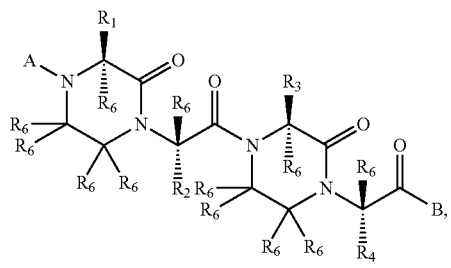

I wherein:

each of $R_1$, $R_2$, $R_3$, and $R_4$ is independently an amino acid side chain, H, N(R)$_2$, OR, halogen, an alkyl, or an aryl; wherein each R is independently H, an alkyl, or an aryl;

each $R_6$ is independently H, N(R)$_2$, OR, halogen, an alkyl, or an aryl; wherein each R is independently H, an alkyl, or an aryl;

A is $X_1$ or C, wherein:

$X_1$ is H, COR', CO$_2$R', CONHR', an alkyl, an aryl, an arylalkyl, a cycloalkyl, a heteroaryl, a protecting group for protection of an amine, a targeting moiety, or a tag; wherein R' is H, an alkyl, an aryl, an arylalkyl, a cycloalkyl, a heteroaryl, a targeting moiety, or a tag; and C is a moiety of the formula

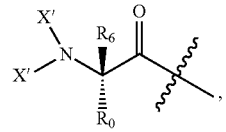

wherein:

each X' is independently H, COR', CO$_2$R', CONHR', N(R")$_2$, an alkyl, an aryl, an arylalkyl, a cycloalkyl, a heteroaryl, a targeting moiety, or a tag; wherein:

R' is H, an alkyl, an aryl, an arylalkyl, a cycloalkyl, a heteroaryl, a targeting moiety, or a tag; and each R" is independently H, an alkyl, an aryl, an arylalkyl, a cycloalkyl, a heteroaryl, a targeting moiety, or a tag;

$R_0$ is an amino acid side chain, H, $N(R)_2$, OR, halogen, an alkyl, or an aryl;

wherein each R is independently H, an alkyl, or an aryl; and $R_6$ is H, $N(R)_2$, OR, halogen, an alkyl, or an aryl; wherein each R is independently H, an alkyl, or an aryl; and B is OR', COR', $N(R''')_2$, an alkyl, an aryl, an arylalkyl, a cycloalkyl, a heteroaryl, a protecting group for protection of a carboxylic acid, a targeting moiety, or a tag; wherein:

R' is H, an alkyl, an aryl, an arylalkyl, a cycloalkyl, a heteroaryl, a targeting moiety, or a tag; and each R''' is independently H, $CO_2R'$, CONHR', an alkyl, an aryl, an arylalkyl, a cycloalkyl, a heteroaryl, a targeting moiety, or a tag;

and wherein:

(i) A is $X_1$, $R_1$ and $R_2$ are hydrophobic and $R_4$ is a hydrogen bond acceptor or hydrogen bond donor, with the proviso that at least one of the following conditions is not met: $R_1$ is a leucine side chain, $R_2$ is a leucine side chain, and $R_4$ is a glutamine side chain;

(ii) A is a moiety of formula

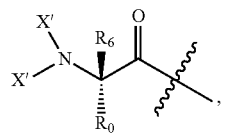

$R_0$ and $R_3$ are hydrophobic, and $R_4$ is a hydrogen bond acceptor or hydrogen bond donor, with the proviso that at least one of the following conditions is not met: $R_1$ is a leucine side chain, $R_2$ is a leucine side chain, and $R_4$ is a glutamine side chain, and with the proviso that the compound is not a compound of formula

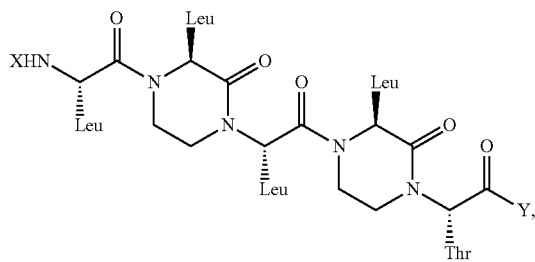

where X is H, $COCH_3$, or any amino acid, and Y is OH, $NH_2$, OMe, or any amino acid;

(iii) the oligooxopiperazine is BB2-125; or (iv) the oligooxopiperazine is BB2-164.

2. The oligooxopiperazine according to claim 1, wherein A is $X_1$, $R_1$ and $R_2$ are hydrophobic, and $R_4$ is a hydrogen bond acceptor or hydrogen bond donor.

3. The oligooxopiperazine according to claim 1, wherein A is a moiety of formula

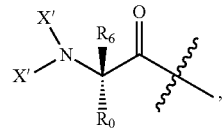

$R_0$ and $R_3$ are hydrophobic, and $R_4$ is a hydrogen bond acceptor or hydrogen bond donor.

4. The oligooxopiperazine according to claim 1, wherein the oligooxopiperazine is BB2-164.

5. A pharmaceutical formulation comprising:
an oligooxopiperazine according to claim 1 and
a pharmaceutically acceptable vehicle.

6. The pharmaceutical formulation according to claim 5, wherein A is $X_1$, $R_1$ and $R_2$ are hydrophobic, and $R_4$ is a hydrogen bond acceptor or hydrogen bond donor.

7. The pharmaceutical formulation according to claim 5, wherein A is a moiety of formula

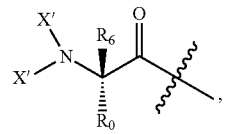

$R_0$ and $R_3$ are hydrophobic, and $R_4$ is a hydrogen bond acceptor or hydrogen bond donor.

8. The pharmaceutical formulation according to claim 5, wherein the oligooxopiperazine is BB2-164.

9. The oligooxopiperazine according to claim 1, wherein:

(i) when A is $X_1$, $X_1$ is H, COR', $CO_2R'$, an alkyl, an aryl, an arylalkyl, a cycloalkyl, a heteroaryl, a protecting group for protection of an amine, a targeting moiety, or a tag; wherein R' is H, an alkyl, an aryl, an arylalkyl, a cycloalkyl, a heteroaryl, a targeting moiety, or a tag;

(ii) when A is C, each X' is independently H, COR', $CO_2R'$, $N(R'')_2$, an alkyl, an aryl, an arylalkyl, a cycloalkyl, a heteroaryl, a targeting moiety, or a tag; wherein:

R' is H, an alkyl, an aryl, an arylalkyl, a cycloalkyl, a heteroaryl, a targeting moiety, or a tag; and each R" is independently H, an alkyl, an aryl, an arylalkyl, a cycloalkyl, a heteroaryl, a targeting moiety, or a tag; and (iii) when B is $N(R''')_2$, each R''' is independently H, $CO_2R'$, an alkyl, an aryl, an arylalkyl, a cycloalkyl, a heteroaryl, a targeting moiety, or a tag.

10. An oligooxopiperazine, wherein the oligooxopiperazine is BB2-125.

11. A pharmaceutical formulation comprising:
the oligooxopiperazine of claim 10 and
a pharmaceutically acceptable vehicle.

* * * * *

SEQUENCE LISTING

```
<160> NUMBER OF SEQ ID NOS: 6

<210> SEQ ID NO 1
<211> LENGTH: 51
<212> TYPE: PRT
<213> ORGANISM: Homo sapiens

<400> SEQUENCE: 1

Ser Asp Leu Ala Cys Arg Leu Leu Gly Gln Ser Met Asp Glu Ser Gly
1               5                   10                  15

Leu Pro Gln Leu Thr Ser Tyr Asp Cys Glu Val Asn Ala Pro Ile Gln
            20                  25                  30

Gly Ser Arg Asn Leu Leu Gln Gly Glu Glu Leu Leu Arg Ala Leu Asp
        35                  40                  45

Gln Val Asn
    50

<210> SEQ ID NO 2
<211> LENGTH: 8
<212> TYPE: PRT
<213> ORGANISM: Artificial
<220> FEATURE:
<223> OTHER INFORMATION: Alpha-helix

<400> SEQUENCE: 2

Glu Leu Leu Arg Ala Leu Asp Gln
1               5

<210> SEQ ID NO 3
<211> LENGTH: 29
<212> TYPE: PRT
<213> ORGANISM: Artificial
<220> FEATURE:
<223> OTHER INFORMATION: Signal peptide
```

```
<400> SEQUENCE: 3

Met Met Ser Phe Val Ser Leu Leu Leu Val Gly Ile Leu Phe Tyr Ala
1               5                   10                  15

Thr Glu Ala Glu Gln Leu Thr Lys Cys Glu Val Phe Gln
            20                  25

<210> SEQ ID NO 4
<211> LENGTH: 4
<212> TYPE: PRT
<213> ORGANISM: Artificial
<220> FEATURE:
<223> OTHER INFORMATION: Retention signal

<400> SEQUENCE: 4

Lys Glu Asp Leu
1

<210> SEQ ID NO 5
<211> LENGTH: 8
<212> TYPE: PRT
<213> ORGANISM: Artificial
<220> FEATURE:
<223> OTHER INFORMATION: Nuclear transport peptide

<400> SEQUENCE: 5

Pro Pro Lys Lys Lys Arg Lys Val
1               5

<210> SEQ ID NO 6
<211> LENGTH: 25
<212> TYPE: PRT
<213> ORGANISM: Artificial
<220> FEATURE:
<223> OTHER INFORMATION: Mitochondrial transport peptide

<400> SEQUENCE: 6

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25
```